United States Patent
Lub et al.

(10) Patent No.: US 9,969,932 B2
(45) Date of Patent: May 15, 2018

(54) CLASS OF GREEN/YELLOW EMITTING PHOSPHORS BASED ON BENZOXANTHENE DERIVATIVES FOR LED LIGHTING

(71) Applicant: PHILIPS LIGHTING HOLDING B.V., Eindhoven (NL)

(72) Inventors: Johan Lub, Valkenswaard (NL); Rifat Ata Mustafa Hikmet, Eindhoven (NL); Dirk Veldman, Eindhoven (NL)

(73) Assignee: PHILIPS LIGHTING HOLDING B.V., Eindhoven (NL)

( * ) Notice: Subject to any disclaimer, the term of this patent is extended or adjusted under 35 U.S.C. 154(b) by 254 days.

(21) Appl. No.: 14/771,666

(22) PCT Filed: Feb. 14, 2014

(86) PCT No.: PCT/EP2014/052887
§ 371 (c)(1),
(2) Date: Aug. 31, 2015

(87) PCT Pub. No.: WO2014/131628
PCT Pub. Date: Sep. 4, 2014

(65) Prior Publication Data
US 2016/0017219 A1    Jan. 21, 2016

(30) Foreign Application Priority Data

Mar. 1, 2013 (EP) ..................... 13157359

(51) Int. Cl.
*C09K 11/06* (2006.01)
*C07D 491/052* (2006.01)
(Continued)

(52) U.S. Cl.
CPC .......... *C09K 11/06* (2013.01); *C07D 491/052* (2013.01); *C09B 5/62* (2013.01);
(Continued)

(58) Field of Classification Search
None
See application file for complete search history.

(56) References Cited

U.S. PATENT DOCUMENTS 3,748,330 A    7/1973 Fuchs
3,812,051 A    5/1974 Merkle et al.
(Continued)

FOREIGN PATENT DOCUMENTS

DE    1569761 A1    6/1970
FR    2089620 A5    1/1972
(Continued)

OTHER PUBLICATIONS

Machine English translation of Kiyoyanagi et al. (JP 2003-217857 A). Jul. 8, 2017.*

*Primary Examiner* — J. L. Yang

(57) ABSTRACT

The invention provides a lighting device (1) comprising (a) a light source (10) configured to generate light source light (11), and (b) a light converter (100) configured to convert at least part of the light source light (11) into visible converter light (111), wherein the light converter (100) comprises a matrix (120) containing an organic luminescent material (140) of the benzoxanthene derivative type. The lighting device may further comprise a further luminescent material (130).

12 Claims, 8 Drawing Sheets

(51) Int. Cl.
    *F21K 99/00*     (2016.01)
    *C09K 11/02*     (2006.01)
    *C09K 11/08*     (2006.01)
    *C09B 57/14*     (2006.01)
    *C09K 11/77*     (2006.01)
    *H05B 33/14*     (2006.01)
    *H01L 51/00*     (2006.01)
    *C09B 5/62*     (2006.01)
    *C09B 67/22*     (2006.01)
    *F21K 9/64*     (2016.01)
    *H01L 51/50*     (2006.01)

(52) U.S. Cl.
    CPC .......... *C09B 57/14* (2013.01); *C09B 67/0033* (2013.01); *C09K 11/025* (2013.01); *C09K 11/0883* (2013.01); *C09K 11/7731* (2013.01); *C09K 11/7734* (2013.01); *F21K 9/64* (2016.08); *H01L 51/0053* (2013.01); *H01L 51/0071* (2013.01); *H05B 33/14* (2013.01); *C09K 2211/1007* (2013.01); *C09K 2211/1014* (2013.01); *C09K 2211/1022* (2013.01); *C09K 2211/1033* (2013.01); *C09K 2211/1044* (2013.01); *C09K 2211/1096* (2013.01); *H01L 51/5036* (2013.01)

(56) References Cited

U.S. PATENT DOCUMENTS

| | | |
|---|---|---|
| 4,845,223 A | 7/1989 | Seybold et al. |
| 6,537,679 B1 | 3/2003 | Buoni et al. |
| 2003/0111649 A1 | 6/2003 | Park et al. |
| 2012/0119639 A1* | 5/2012 | Staats .................... C09K 11/06 313/485 |

FOREIGN PATENT DOCUMENTS

| | | |
|---|---|---|
| JP | 2003217857 A * | 7/2003 |
| WO | 02055570 A1 | 7/2002 |
| WO | 2010116294 A1 | 10/2010 |
| WO | 2011031871 A1 | 3/2011 |
| WO | 2012113884 A1 | 8/2012 |
| WO | 2012140542 A1 | 10/2012 |

* cited by examiner

US 9,969,932 B2

CLASS OF GREEN/YELLOW EMITTING PHOSPHORS BASED ON BENZOXANTHENE DERIVATIVES FOR LED LIGHTING

CROSS-REFERENCE TO PRIOR APPLICATIONS

This application is the U.S. National Phase application under 35 U.S.C. § 371 of International Application No. PCT/EP2014/052887, filed on Feb. 14, 2014, which claims the benefit of European Patent Application No. EP13157359.4, filed on Mar. 1, 2013. These application are hereby incorporated by reference herein.

FIELD OF THE INVENTION

The invention relates to a lighting device comprising (a) a light source configured to generate light source light, and (b) a light converter configured to convert at least part of the light source light into visible converter light. The invention further pertains to such light converter per as well as to an organic luminescent material that can comprised by such light converter.

BACKGROUND OF THE INVENTION

Phosphor-enhanced light sources are known per se and are used for substantially all kinds of light sources. Phosphor-enhanced light sources comprise a light emitter and a luminescent material. The luminescent material is arranged for converting at least part of the light emitted by the light emitter into light of a longer wavelength.

Well-known phosphor-enhanced light sources are, for example, mercury vapor discharge lamps in which the light is emitted from a discharge in which the presence of mercury vapor causes the discharge to emit ultraviolet radiation. At least a part of the ultraviolet radiation is absorbed by a luminescent material and converted into light of a longer wavelength which is subsequently emitted by the luminescent material. Such mercury vapor discharge lamp may, for example, comprise a discharge vessel in which the discharge is generated. The luminescent material is typically applied to the inner wall of the discharge vessel such that the ultraviolet radiation emitted by the discharge does not need to pass the discharge vessel but is inside the discharge vessel converted into, for example, visible light.

Alternatively, the phosphor-enhanced light source may comprise a solid-state light emitter as the light emitter. Such a solid-state light emitter may, for example, be a light emitting diode, or a laser diode, or an organic light emitting diode. The light emitted by a solid-state light emitter typically has a relatively narrow spectrum arranged around a center wavelength. The width of the spectrum may, for example, be defined by the Full Width Half Maximum (further also indicated as FWHM) of the emission peak which is a width of the emission peak measured at an intensity being half the maximum emission intensity of the light emitted by the solid-state light emitter. The FWHM of a typical emission spectrum of the solid-state light emitter is less than 30 nanometer, which is typically identified by the human eye as light of a single color.

To change the color of the light emitted by the solid-state light emitter, luminescent materials may be added to generate a phosphor-enhanced light source. The luminescent material may, for example, be applied as a layer on top of the (LED) die of the solid-state light emitter, or may, for example, be dispersed in a matrix which may be located at a distance of the solid-state light emitter, a so called "remote phosphor" arrangement. The luminescent material may also be part of a mixture of different luminescent materials, for example, each generating a different color such that the mixed light, for example, generates white light having a specific color temperature. Furthermore, luminescent materials may be added to solid-state light emitters to improve the color rendering characteristics of the solid-state light emitters, as the typical emission characteristic of the luminescent materials is a relatively broad spectrum of light.

The use of dyes in matrices is (also) known in the art. U.S. Pat. No. 6,537,679, for instance, describes a fluorescent retro reflective article comprising a polymer resin comprising poly(1,4-cyclohexanedimethanol-co-ethylene terephthalate) (PETG) and a fluorescent dye selected from the group consisting of perylene imide and perylene ester dyes, thioxanthene dyes, benzoxanthene dyes, and benzothiazine dyes. The PETG fluorescent resin matrix can be used to enhance daytime visibility of a roadway marker. Such a pavement marker comprises a base member comprising a structure of a light-transmissible fluorescent material, the structure having a top surface and a front edge surface, the base member being configured to provide an air cap beneath the structure.

SUMMARY OF THE INVENTION

Efficiency of white emitting light solid state light sources can still be improved. This can be best done by combining RGB LEDs. However, green LEDs are presently not efficient enough in order to obtain high efficiencies. For this reason, phosphor converted (PC) LEDs are suggested for obtaining white light. With the blue LED's as primary source a red and yellow luminescent phosphors are needed. These phosphors should be stable under blue light irradiation conditions during the lifetime of the complete light source (for example TL-retrofit tube, operating at elevated temperature, lifetime of at least 50.000 hours). The use of yellow organic phosphors derived from perylene, such as F170 (2-(2,6-diisopropylphenyl)-1,3-dioxo-2,3-dihydro-1H-benzo[5,10]anthra[2,1,9-def]isoquinoline-8-carbonitrile; CAS Registry no. 936212-95-2 and 676363-16-9) or F83 (diisobutyl 4-cyano-10-isocyanoperylene-3,9-dicarboxylate mixture with diisobutyl 4-cyano-9-isocyanoperylene-3,10-dicarboxylate; CAS Registry no. 100443-95-6), and of Solvent Yellow 98 (2-octadecyl-1H-thioxantheno[2,1,9-def]isoquinoline-1,3(2H)-dione; CAS Registry no. 12671-74-8) or Disperse Yellow (7-(diethylamino)-3-(6-methylbenzo[d]oxazol-2-yl)-2H-chromen-2-one; CAS Registry no. 34564-13-1), results in low lifetimes. These yellow phosphors degrade too fast for use in lighting applications.

Hence, it is an aspect of the invention to provide an alternative lighting device, and especially an alternative light converter, which preferably further at least partly obviate one or more of above-described drawbacks. It is further an aspect of the invention to provide an alternative organic luminescent material, especially emitting in the green and/or yellow, especially for combination with a blue light source, such as a blue LED, which preferably further at least partly obviates one or more of above-described drawbacks.

Here we propose organic phosphors with a similar structure to Solvent Yellow 98 but with the sulfur atom replaced by oxygen, so called benzoxanthene derivatives. The specific systems proposed exhibit much longer lifetimes under the irradiation conditions than known similar prior art systems. Preferentially, the yellow and/or green (and red)

emitting phosphors are in the remote phosphor configuration which may lead to a total increase in the system efficacy. This configuration is most suitable in low power low operating temperature applications such as TLED (tube LED configuration, e.g. LEDs implement in a T8 tube (known in the art of fluorescent lighting)).

Hence, in a first aspect, the invention provides a lighting device comprising (a) a light source configured to generate light source light, (b) a light converter configured to convert at least part of the light source light into visible converter light, wherein the light converter comprises a matrix containing an organic luminescent material as defined by formula (I) (wherein the organic luminescent material is especially configured to provide green and/or yellow light), and (c) optionally a further luminescent material (especially configured to provide at least red light), with the organic luminescent material according to formula (I):

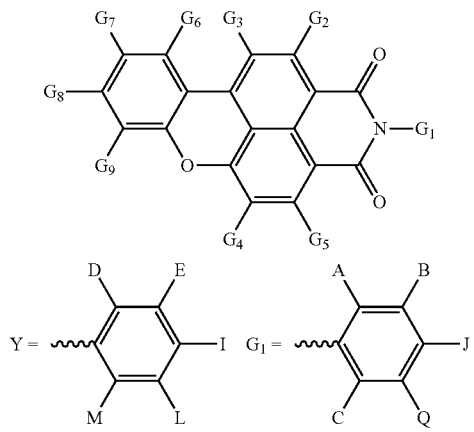

I with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl; and in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl.

In a further aspect, the invention also provides a light converter per se. Hence, in a further aspect the invention also provides a light converter comprising a matrix containing an organic luminescent material as defined by formula I (see above), with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; wherein $R_2$ and $R_7$ are independently selected from $C_1$-$C_{18}$alkyl, $C_6$-$C_{24}$aryl, and $C_6$-$C_{24}$heteroaryl; in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl. As will be elucidated below, such matrix may also comprise one or more further luminescent materials, like quantum dot based materials and/or nitride based materials, and/or other organic luminescent materials, etc., that may especially luminesce in the red.

In yet a further aspect, the invention also provides such organic luminescent material per se. Hence, in a further aspect, the invention also provides an organic luminescent material as defined by formula I (see above), with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_1$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl; in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl; and wherein in a specific embodiment optionally (i) one or both of $G_3$ and $G_4$ are independently selected from $R_3$ and $OR_3$, wherein $R_3$=Y, with D, E, I, L and M independently being selected from hydrogen, halogen, $R_5$, $OR_5$, $NHR_5$, and $NR_6R_5$, wherein $R_5$ and $R_6$ are independently selected from $C_1$-$C_{18}$alkyl, $C_6$-$C_{24}$aryl, and $C_6$-$C_{24}$heteroaryl, and wherein optionally (ii) $G_8$ does not include an amine group. Hence, in embodiments, which may relate to one or more of the lighting device, the light converter and the organic luminescent material per se, one or more of $G_2$-$G_9$ are independently selected from $R_3$, $OR_3$, $NHR_3$, and $NR_4R_3$, wherein $R_3$=Y, with D, E, I, L and M independently being selected from hydrogen, halogen, $R_5$, $OR_5$, $NHR_5$, and $NR_6R_5$, wherein $R_5$ and $R_6$ are independently selected from $C_1$-$C_{18}$alkyl, $C_6$-$C_{24}$aryl, and $C_6$-$C_{24}$heteroaryl.

It appears that such lighting device, light converter and/or organic luminescent material, as defined above, and as further elucidated below, may be applied efficiently and with a good life time under (blue) irradiation. Relative to prior art systems, a 10-100 fold increase in life time was observed.

Herein, the term "$C_1$-$C_{18}$alkyl" may relate to a branched $C_1$-$C_{18}$alkyl or an unbranched $C_1$-$C_{18}$alkyl. The term "$C_1$-$C_{18}$alkyl" may relate to an unsubstituted $C_1$-$C_{18}$alkyl or substituted $C_1$-$C_{18}$alky (i.e. $C_1$-$C_{18}$alkyl with one or more substituents). The term "$C_1$-$C_{18}$alkyl" may relate to a linear $C_1$-$C_{18}$alkyl or non-linear $C_1$-$C_{18}$alkyl (which may be substituted or unsubstituted). The term "non-linear" herein may refer to cyclic, like $C_1$-$C_{18}$ cyclo alkyl.

Herein, the term "$C_2$-$C_{18}$alkyl" may relate to a branched $C_2$-$C_{18}$alkyl or an unbranched $C_2$-$C_{18}$alkyl. The term "$C_2$-$C_{18}$alkyl" may relate to an unsubstituted $C_2$-$C_{18}$alkyl or substituted $C_2$-$C_{18}$alky (i.e. $C_2$-$C_{18}$alkyl with one or more substituents). The term "$C_2$-$C_{18}$alkyl" may relate to a linear $C_2$-$C_{18}$alkyl or non-linear $C_2$-$C_{18}$alkyl (which may be substituted or unsubstituted). The term "non-linear" herein may refer to cyclic, like $C_2$-$C_{18}$ cyclo alkyl.

By way of example, the term "$C_1$-$C_{18}$alkyl" may relate in an embodiment to a linear heptyl group, but may in another embodiment relate to a methyl substitute cyclo hexane group, with one or more fluor substituents. $C_1$-$C_{18}$alkyl especially relates to $C_1$-$C_{16}$ alkyl, like $C_1$-$C_8$ alkyl, such as $C_1$-$C_4$ alkyl.

Examples of alkyl groups are especially methyl, ethyl, n-propyl, isopropyl, n-butyl, isobutyl, sec-butyl, tert-butyl, n-pentyl, neo-pentyl, n-hexyl, n-heptyl, n-octyl, n-nonyl, n-decyl, n-undecyl, n-dodecyl, etc. Examples of cyclo alkyl groups are e.g. cyclopentyl, cyclohexyl, cycloheptyl, cyclooctyl, etc.

Optionally, the carbon chains of the $C_1$-$C_{18}$alkyl and/or $C_2$-$C_{18}$alkyl may be interrupted by one or more groups which are independently selected from —O— and —S—. Hence, in an embodiment the term $C_1$-$C_{18}$ alkyl may also relate to an ether or in a variant a polyether. Therefore, in a specific embodiment $C_1$-$C_{18}$alkyl may also refer to $C_1$-$C_{18}$alkyl comprising one or more ether groups, such as $C_nH_{2n+1}O_m$, with n being an integer from 1 to 18, such as 1-16, and with $0 \le m \le n/2$.

As for instance A, B, C, J, Q may independently relate to $OR_1$, $G_2$-$G_9$ may independently relate to $OR_3$, and D, E, I, L and M may independently relate to $OR_5$, $C_{1-18}$alkyl may thus be part of an alkoxy group. For instance, "A" (in $G_1$) may be methoxy, etc.

Substituents that may be applied may be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the $C_1$-$C_{18}$alkyl is substituted with one or more fluorine atoms. For instance, in an embodiment $C_1$-$C_{18}$alkyl especially relates to $C_nH_{2n+1-m}F_m$ with n being an integer from 1 to 18, such as 1-16, and with $0 \le m \le 2n+1$. Hence, the term "alkyl" and similar terms, may also relate to a substituted alkyl, such as an alkyl that is fluorinated with one or more fluor substituents.

Herein, the term "$C_6$-$C_{24}$aryl" may refer to a mono cyclic aromatic aryl group or to a polycyclic aromatic aryl group. The term "$C_6$-$C_{24}$aryl" may relate to an unsubstituted $C_6$-$C_{24}$aryl or to a substituted $C_6$-$C_{24}$aryl (i.e. $C_6$-$C_{24}$aryl with one or more substituents). $C_6$-$C_{24}$aryl especially relates to $C_6$-$C_{16}$ aryl, like $C_6$-$C_{10}$ aryl. The $C_6$-$C_{24}$aryl may in addition to at least one aryl group, also comprise one or more non-conjugated cyclic groups.

Examples of aryl groups are phenyl, naphthyl, indenyl, fluorenyl, anthracenyl, phenanthrenyl, naphthacenyl, etc. In case the $C_6$-$C_{24}$ aryl comprises one or more aromatic groups and one or more alkyl groups, like methyl phenyl ($C_7$), or ethyl phenyl ($C_8$), the alkyl groups may especially be linear alkyl groups. Also these alkyl groups may independently comprise one or more substituents. Further, also these alkyl groups may be interrupted by one or more groups which are independently selected from —O— and —S—. Hence, in an embodiment such alkyl group may also relate to an ether or in a variant a polyether.

Substituents that may be applied may be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the $C_6$-$C_{24}$aryl is substituted with one or more fluorine atoms.

Herein, the term "$C_6$-$C_{24}$heteroaryl" may refer to heteroaromatic, mono- or polycyclic groups. The term "$C_6$-$C_{24}$heteroaryl" may relate to an unsubstituted $C_6$-$C_{24}$heteroaryl or to a substituted $C_6$-$C_{24}$heteroaryl (i.e. $C_6$-$C_{24}$heteroaryl with one or more substituents). $C_6$-$C_{24}$ heteroaryl especially relates to $C_6$-$C_{16}$ heteroaryl, like $C_6$-$C_{10}$ heteroaryl The $C_6$-$C_{24}$heteroary may in addition to at least one heteroaryl group, also comprise one or more non-conjugated cyclic groups.

Examples of $C_6$-$C_{24}$heteroyaryls are e.g. 2,5-indenylene, 2,6-indenylene, pyrazinylene, pyridinylene, pyrimidinylene, 2,4-thiophenylene, 2,5-thiophenylene, 1,3,4-thiadiazol-2,5-ylene, 1,3-thiazol-2,4-ylene, 1,3-thiazol-2,5-ylene, 1,3-oxazol-2,4-ylene, 1,3-oxazol-2,5-ylene, 1,3,4-oxadiazol-2,5-ylene, etc. In case the $C_6$-$C_{24}$heteroaryl comprises one or more hetero aromatic groups and one or more alkyl groups, the alkyl groups may especially be linear alkyl groups. Also these aklyl groups may independently comprise one or more substituents. Further, also these alkyl groups may be interrupted by one or more groups which are independently selected from —O— and —S—. Hence, in an embodiment such alkyl group may also relate to an ether or in a variant a polyether.

Substituents that may be applied may be selected from fluorine, chlorine, hydroxyl, cyano, acyl, COOH, carboxylate, alkylcarbonyloxy, carbamoyl, alkylaminocarbonyl, (dialkylamino)carbonyl, $SO_3H$, sulfonate, sulfoamino, sulfamide, sulfamoyl, and amidino. In general, the substituents will be limited to 1-6 substituents, like 1-4 substituents. In a specific embodiment, the $C_6$-$C_{24}$heteroaryl is substituted with one or more fluorine atoms.

In an embodiment, wherein one or more of $R_1$, $R_2$, $R_3$, $R_4$, $R_5$, $R_6$, $R_7$ are available, one or more of these are independently selected from the group consisting of (i) $C_nH_{2n+1}O_m$, with n being an integer from 1 to 18 and with $0 \le m \le n/2$, (ii) $C_nH_{2n+1-m}F_m$ with n being an integer from 1 to 18 and with $0 \le m \le 2n+1$, (iii) $C_6$-$C_{24}$aryl comprising one or more ether groups, (iv) $C_6$-$C_{24}$aryl comprising one or more fluor substituents, (v) $C_6$-$C_{24}$heteroaryl comprising one or more ether groups, and (vi) $C_6$-$C_{24}$heteroaryl comprising one or more fluor substituents.

Halogens herein are especially fluorine, chlorine, even more especially fluorine. Especially, when one or more halogens are present, the one or more halogens comprise (only) fluorine.

The phrase "independently selected from" may indicate that any of the indicated species may be chosen, independent of the other choices. For instance, in theory $G_2$ might be hydrogen, $G_3$ fluorine, $G_4$ $C_1$-$C_{18}$alkyl, $G_5$ $OR_3$ with $R_3$ being $C_1$-$C_{18}$alkyl, $G_6$ $NR_4R_3$, with $R_3$ being $C_1$-$C_{18}$alkyl and with $R_4$ being $C_6$-$C_{24}$aryl, $G_7$ $C_6$-$C_{24}$heteroaryl, $G_8$ and $G_9$ halogen substituted $C_1$-$C_{18}$alkyl. In general however, at least four of $G_2$-$G_9$ are hydrogen, and at least two, especially at least three of A, B, C, J, Q are hydrogen. Further, when $R_3$=Y, especially at least two, more especially at least three of D, E, I, L, M are hydrogen.

In an embodiment, $G_8$ does not include an amine group. The absence of such amine group may be beneficial for stability. Especially, a covalent bond between the phenyl C directly to a primary, secondary or tertiary amine may be avoided. Optionally, the $G_8$ group or radical may also not comprise an amide group. In a specific embodiment, $G_8$ is selected from hydrogen, halogen, $R_3$, and $OR_3$, wherein $R_3$ and $R_4$ are independently selected from $C_1$-$C_{18}$alkyl, $C_6$-$C_{24}$aryl, and $C_6$-$C_{24}$heteroaryl, wherein $R_3$ and $R_4$ especially do not comprise an amine group. Especially, $G_8$ comprises hydrogen or halogen.

Good optical results in terms of stability and/or efficiency and/or spectral distribution of the emission can be obtained with one or more of isopropyl and tertbutyl groups associated to $G_1$. Hence, in a specific embodiment one, or especially two of A, B, and C are independently selected from the group consisting of isopropyl and tertbutyl. In a specific embodiment, A and C are isopropyl, and $G_2$, $G_5$, $G_7$-$G_9$, B, J and Q are hydrogen. Yet in another embodiment, B and C are tertbutyl, and $G_2$, $G_5$, $G_7$-$G_9$, A, J and Q are hydrogen.

Further, alternatively or additionally substitution of $G_3$ and/or $G_4$ with an aryl or aryloxy (i.e. —O-aryl, such as $OR_3$, wherein $R_3$=Y) group provides good organic luminescent materials. Hence, in an embodiment one or both of $G_3$ and $G_4$ are independently selected from $R_3$ and $OR_3$, wherein $R_3$=Y (see chemical formulas above), with D, E, I, L and M independently being selected from hydrogen, halogen, $C_1$-$C_{18}$alkyl, $C_6$-$C_{24}$aryl, and $C_6$-$C_{24}$heteroaryl. Especially, D, E, I, L and M are independently being selected from hydrogen and halogen, especially hydrogen and fluorine, even more especially hydrogen. Hence, in a specific embodiment, one or both of $G_3$ and $G_4$ are independently selected from $R_3$ and $OR_3$, wherein $R_3$=Y, with D, E, I, L and M being hydrogen.

In a specific embodiment, one or both of $G_3$ and $G_4$ are independently selected from $R_3$ and $OR_3$, wherein $R_3$=Y, with D, E, I, L and M being hydrogen, and wherein $G_2$, $G_5$, $G_7$-$G_9$, J and Q are hydrogen. Especially $R_3$=Y, with D, E, I, L and M being hydrogen.

In an embodiment, one or more of $G_2$-$G_9$ may independently also comprise an oxygen-containing alkyl group $C_nH2_{n+1}O_m$, n being an integer from 1 to 16 and $0 \leq m \leq n/2$, such as an ether or alcohol, especially an ether. Alternatively or additionally, one or more of D, E, I, L and M may independently also comprise an oxygen-containing alkyl group $C_nH2_{n+1}O_m$, n being an integer from 1 to 16 and $0 \leq m \leq n/2$. Especially, minimally two of D, E, I, L and M groups are hydrogen atoms. Further, in a specific embodiment $G_3$ is a $C_6H_5O$— group and $G_2$, $G_4$-$G_9$ is hydrogen. In yet another embodiment, $G_2$-$G_9$ is hydrogen.

In a specific embodiment, each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms.

Further, as will be elucidated below the matrix may especially comprise an aromatic polyester, or a copolymer thereof such as e.g. polyglycolide or polyglycolic acid (PGA), polylactic acid (PLA), polycaprolactone (PCL), polyethylene adipate (PEA), polyhydroxy alkanoate (PHA), polyhydroxy butyrate (PHB), poly(3-hydroxybutyrate-co-3-hydroxyvalerate) (PHBV), polyethylene terephthalate (PET), polybutylene terephthalate (PBT), polytrimethylene terephthalate (PTT), polyethylene naphthalate (PEN); especially, the matrix may comprise polyethylene terephthalate (PET). Further, as will also be elucidated below the matrix may comprise a further luminescent material embedded in the matrix.

As indicated above, organic phosphors (organic luminescent materials) may suffer from a relatively low photochemical stability. Their stability may strongly depend on the temperature of the material and on the amount of light that it converts. For this reason, organic phosphors may be suitable candidates when used in the remote configuration (see below). A lighting assembly using organic remote phosphor is relatively cheap because of the use of relatively cheap organic luminescent material. Furthermore, organic luminescent materials allow an easy design of a specific organic luminescent material which has a light emission spectrum anywhere in visible spectrum. Such molecules can be synthesized and depending on the molecular structure it emits a specific light.

The above described organic luminescent material is of the benzoxanthene derivative type. Benzoxanthene derivative are known in the art and are for instance described in U.S. Pat. No. 3,748,330.

The above described organic luminescent material may be well excitable in the blue and/or UV.

The term "organic luminescent material" may especially refer to an organic material that has luminescent properties (i.e. can emit light upon excitation (by one or more of UV and blue light)). As the organic luminescent material of formula I emits especially at least in the green and/or yellow, the organic luminescent material is herein also indicated as green and/or yellow emitter or green and/or yellow emitting luminescent material or green and/or yellow luminescent material. However, the organic luminescent material of formula I may also remit in e.g. the red.

The organic luminescent material may be applied in the lighting device as defined herein. Such lighting device may for instance comprise a TLED (tube with LED(s) within the tube, such as a T8 tube), which is a kind of retrofit lamp. The organic luminescent material may also be applied in a light bulb with LED(s) within the bulb, which is a kind of retrofit incandescent lamp. In both cases, the organic luminescent material may be applied remote, such as on the upstream face of the transmissive envelope (i.e. the inner face of the transmissive envelope.

Optionally, the matrix may be used as transmissive envelope of a lighting device; in other words: the transmissive envelope substantially consists of the matrix.

The term light converter may refer to a system that is configured to convert light from a first wavelength into light of a second wavelength. Especially, UV and/or blue light (excitation wavelength) may be (at least partially) converted into visible light (of higher wavelength than the excitation wavelength). Another term for "light converter" is "wavelength converter".

The light converter may be in the form of for instance particles, flakes, a film, a plate, etc. In a specific embodiment, the term light converter may include a self-supporting layer.

Hence, in an embodiment, the light converter is selected from the group consisting of a coating, a self-supporting layer, and a plate; which light converter is thus especially solid at room temperature, especially even up to 100° C., especially even up to 150° C., more especially even up to 200° C. The light converter may be flexible or may be rigid. Further, the light converter may be flat or curved (in one or two dimensions). Further, optionally the light converter may comprise outcoupling structures at at least part of the external surface of the light converter.

The light converter may comprise one or more parts, like layers on top of each other. Such parts may comprise different luminescent materials or luminescent materials in different concentration. However, at least part of the light converter comprises the (red) organic luminescent material.

The matrix may especially comprise a matrix material and the above indicated materials such as the organic luminescent material, and optionally further luminescent material, etc. The organic luminescent material(s) and optionally other luminescent materials may in an embodiment especially be evenly distributed throughout the matrix. However, the light converter may also comprise two or more segments, wherein two or more segments have different compositions at least with respect to the luminescent material(s), e.g. with respect to type and/or concentration of the luminescent material(s).

The luminescent material(s) (i.e. at least the organic luminescent material according to formula I, but optionally also including one or more further luminescent materials), may in an embodiment molecularly be distributed through the matrix. Alternatively or additionally, the luminescent material(s) are available as particles, optionally having a coating. In the latter embodiment, coated particles may be embedded in the matrix. The coating may especially be applied to seal such particle from $H_2O$ and/or $O_2$.

Especially, the matrix material is transmissive for light having a wavelength selected from the range of 380-750 nm. For instance, the matrix material may be transmissive for blue, and/or green, and/or red light. Especially, the matrix material is transmissive for at least the entire range of 420-680 nm. Especially, the matrix material may have a light transmission in the range of 50-100%, especially in the range of 70-100%, for light generated by the light source of the lighting unit (see also below) and having a wavelength selected from the visible wavelength range. In this way, the matrix material is transmissive for visible light from the lighting unit. The transmission or light permeability can be determined by providing light at a specific wavelength with a first intensity to the material and relating the intensity of the light at that wavelength measured after transmission through the material, to the first intensity of the light provided at that specific wavelength to the material (see also E-208 and E-406 of the CRC Handbook of Chemistry and Physics, 69th edition, 1088-1989). The light converter may be transparent or translucent, but may especially be transparent. Especially, the light converter is substantially transparent and/or does not substantially scatter light. When the light converter is transparent, light of the light source may not entirely be absorbed by the light converter. Especially when using blue light, this may be of interest, as the blue light may be used to excite the light luminescent materials and may be used to provide a blue component (in white light).

The matrix (material) may comprises one or more materials selected from the group consisting of a transmissive organic material support, such as selected from the group consisting of PE (polyethylene), PP (polypropylene), PEN (polyethylene napthalate), PC (polycarbonate), polymethylacrylate (PMA), polymethylmethacrylate (PMMA) (Plexiglas or Perspex), cellulose acetate butyrate (CAB), silicone, polyvinylchloride (PVC), polyethylene terephthalate (PET), (PETG) (glycol modified polyethylene terephthalate), PDMS (polydimethylsiloxane), and COC (cyclo olefin copolymer). However, in another embodiment the matrix (material) may comprise an inorganic material. Preferred inorganic materials are selected from the group consisting of glasses, (fused) quartz, transmissive ceramic materials, and silicones. Also hybrid materials, comprising both inorganic and organic parts may be applied. Especially preferred are PMMA, PET, transparent PC, or glass as material for the matrix (material). Even more especially, the matrix comprises polyethylene terephthalate (PET) as this matrix seems to give the best optical properties compared to other matrices with the same luminescent materials(s). The organic luminescent material degrades (under influence of light source irradiation) slowest in PET. Herein, the term "PET" may also refer to PET-G (Polyethylene Terephtalate Glycol-modified or optional other modifications. Hence, the matrix especially comprises a polymeric material, that is especially transmissive for at least part of light generated by the organic luminescent material.

The light converter may especially be made by combining the luminescent material(s) and optionally other ingredients and one or more precursors of the matrix, followed by a synthesis of the matrix. For instance, in case of polymeric matrix materials this may be done by using monomeric precursors of the polymer and polymerizing the monomeric precursors, like by step-growth polymerization, or by radical chain polymerization, etc., in the presence of the luminescent material(s) and optionally other ingredients, to provide the polymeric matrix. Another option may be using as starting material(s) molecules, especially polymers, that are curable, and curing these molecules, especially polymers, in the presence of the luminescent material(s) and optionally other ingredients, to provide the matrix. Hence, especially the matrix is a polymeric matrix.

In a specific embodiment, one or more of $G_1$, $G_2$, $G_3$, $G_4$, $G_5$, $G_6$, $G_7$, $G_8$ and $G_9$, comprise a covalent link with the matrix (material), especially one or more of $G_1$ and $G_8$, comprise a covalent link with the matrix (thus especially a polymeric matrix). This may for instance be obtained by providing one or more of these groups, such as one or more of $G_1$ and $G_6$, with a curable group or a polymerizable group. This may further facilitate embedding the organic luminescent material in the matrix. Hence, in an embodiment, one or more of $G_1$, $G_2$, $G_3$, $G_4$, $G_5$, $G_6$, $G_7$, $G_8$ and $G_9$ may comprise a curable or cross-linkable group.

The matrix may be coated or enclosed by a seal or coating. The coating or seal may especially be applied to seal such matrix from $H_2O$ and/or $O_2$.

As indicated above, the light converter may especially comprise a green and/or yellow luminescent material and optionally also a red luminescent material. The light converter may comprise a plurality of luminescent materials, of which at least one comprises an organic luminescent material according to formula I.

The term "formula (I)" may also be indicated as "chemical formula (I)". However, the light converter may also comprise a plurality of organic luminescent materials according to formula I. Hence, in an embodiment, the term "organic luminescent material" may relate to a combination of different organic luminescent material all complying with formula (I).

Further, the light converter especially comprises an further luminescent material (see further below). However, the light converter may also comprise a plurality of further luminescent materials. Hence, in an embodiment the light converter may comprise one or more organic luminescent materials according to formula I, and optionally one or more other organic luminescent materials, and optionally one or more inorganic luminescent materials. The light converter may further comprise one or more scattering materials, and optionally other materials.

Hence, one or more further luminescent materials may be applied. The one or more further luminescent materials may also be embedded in the light converter. Alternatively or additionally, the one or more further luminescent materials may be available in a coating on the luminescent light converter. Alternatively or additionally, the one or more further luminescent materials may be arranged within the lighting device separate from the light converter. Especially, the one or more further luminescent materials comprise a red emitting phosphor. The term "further luminescent material" especially refers to an inorganic material that has luminescent properties (i.e. can emit light upon excitation (by one or more of UV and blue light)). The further luminescent material may especially be configured to emit at least in the red, though other wavelengths are not excluded, like (also) in the yellow, green, etc. The term "further luminescent material" especially refers to an inorganic material that has luminescent properties (i.e. can emit light upon excitation (by one or more of UV and blue light)). However, the further luminescent material may in other embodiments comprise an organic luminescent material (different from the organic luminescent material(s) according to formula I).

Hence, the further luminescent material as indicated above may especially be configured to provide red light (and optionally other light). Hence, the further luminescent material may especially be configured to convert at least part of the light of the light source into at least red light. The further luminescent material, and especially an further luminescent material (configured to provide red light), may be comprised by the light converter, especially the matrix, but may also be outside the light converter, such as a coating on the light converter.

The further luminescent material may comprise quantum dots (QDs). Amongst other narrow band emitters quantum dots are highly suitable for this purpose. Quantum dots are small crystals of semiconducting material generally having a width or diameter of only a few nanometers. When excited by incident light, a quantum dot emits light of a color determined by the size and material of the crystal. Light of a particular color can therefore be produced by adapting the size of the dots. This means that by using quantum dots any spectrum can be obtained as they are narrow band emitters. Most known quantum dots with emission in the visible range are based on cadmium selenide (CdSe) with shell such as cadmium sulfide (CdS) and zinc sulfide (ZnS). Cadmium free quantum dots such as indium phosphide (InP), and copper indium sulfide ($CuInS_2$) and/or silver indium sulfide ($AgInS_2$) can also be used. Quantum dots show very narrow emission band and thus they show saturated colors. Furthermore, the emission color can easily be tuned by adapting the size of the quantum dots.

The quantum dots or luminescent nanoparticles, which are herein indicated as light converter nanoparticles, may for instance comprise group II-VI compound semiconductor quantum dots selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnالسTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe. In another embodiment, the luminescent nanoparticles may for instance be group III-V compound semiconductor quantum dots selected from the group consisting of GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs. In yet a further embodiment, the luminescent nanoparticles may for instance be I-III-VI2 chalcopyrite-type semiconductor quantum dots selected from the group consisting of $CuInS_2$, $CuInSe_2$, $CuGaS_2$, $CuGaSe_2$, $AgInS_2$, $AgInSe_2$, $AgGaS_2$, and $AgGaSe_2$. In yet a further embodiment, the luminescent nanoparticles may for instance be I-V-VI2 semiconductor quantum dots, such as selected from the group consisting of $LiAsSe_2$, $NaAsSe_2$ and $KAsSe_2$. In yet a further embodiment, the luminescent nanoparticles may for instance be a group IV-VI compound semiconductor nano crystals such as SbTe. In a specific embodiment, the luminescent nanoparticles are selected from the group consisting of InP, $CuInS_2$, $CuInSe_2$, CdTe, CdSe, CdSeTe, $AgInS_2$ and $AgInSe_2$. In yet a further embodiment, the luminescent nanoparticles may for instance be one of the group II-VI, III-V, I-III-V and IV-VI compound semiconductor nano crystals selected from the materials described above with inside dopants such as ZnSe:Mn, ZnS:Mn. The dopant elements could be selected from Mn, Ag, Zn, Eu, S, P, Cu, Ce, Tb, Au, Pb, Tb, Sb, Sn and Tl. Herein, the luminescent nanoparticles based luminescent material may also comprise different types of QDs, such as CdSe and ZnSe:Mn.

It appears to be especially advantageous to use II-VI quantum dots. Hence, in an embodiment the semiconductor based luminescent quantum dots comprise II-VI quantum dots, especially selected from the group consisting of CdS, CdSe, CdTe, ZnS, ZnSe, ZnTe, HgS, HgSe, HgTe, CdSeS, CdSeTe, CdSTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe and HgZnSTe, even more especially selected from the group consisting of CdS, CdSe, CdSe/CdS and CdSe/CdS/ZnS.

In an embodiment, Cd-free QDs are applied. In a specific embodiment, the light converter nano-particles comprise III-V QDs, more specifically an InP based quantum dots, such as a core-shell InP—ZnS QDs. Note that the terms "InP quantum dot" or "InP based quantum dot" and similar terms may relate to "bare" InP QDs, but also to core-shell InP QDs, with a shell on the InP core, such as a core-shell InP—ZnS QDs, like a InP—ZnS QDs dot-in-rod.

Typical dots are made of binary alloys such as cadmium selenide, cadmium sulfide, indium arsenide, and indium phosphide. However, dots may also be made from ternary alloys such as cadmium selenide sulfide. These quantum dots can contain as few as 100 to 100,000 atoms within the quantum dot volume, with a diameter of 10 to 50 atoms. This corresponds to about 2 to 10 nanometers. For instance, spherical particles such as CdSe, InP, or $CuInSe_2$, with a diameter of about 3 nm may be provided. The luminescent nanoparticles (without coating) may have the shape of spherical, cube, rods, wires, disk, multi-pods, etc., with the size in one dimension of less than 10 nm. For instance, nanorods of CdSe with the length of 20 nm and a diameter of 4 nm may be provided. Hence, in an embodiment the semiconductor based luminescent quantum dots comprise core-shell quantum dots. In yet another embodiment, the semiconductor based luminescent quantum dots comprise dots-in-rods nanoparticles. A combination of different types of particles may also be applied. For instance, core-shell particles and dots-in-rods may be applied and/or combinations of two or more of the afore-mentioned nano particles may be applied, such as CdS and CdSe. Here, the term "different types" may relate to different geometries as well as to different types of semiconductor luminescent material. Hence, a combination of two or more of (the above indicated) quantum dots or luminescent nano-particles may also be applied.

One example, such as derived from WO 2011/031871, of a method of manufacturing a semiconductor nanocrystal is a colloidal growth process.

In an embodiment, nanoparticles can comprise semiconductor nanocrystals including a core comprising a first semiconductor material and a shell comprising a second semiconductor material, wherein the shell is disposed over at least a portion of a surface of the core. A semiconductor nanocrystal including a core and shell is also referred to as a "core/shell" semiconductor nanocrystal.

For example, the semiconductor nanocrystal can include a core having the formula MX, where M can be cadmium, zinc, magnesium, mercury, aluminum, gallium, indium, thallium, or mixtures thereof, and X can be oxygen, sulfur, selenium, tellurium, nitrogen, phosphorus, arsenic, antimony, or mixtures thereof. Examples of materials suitable for use as semiconductor nanocrystal cores include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing, including ternary and quaternary mixtures or alloys.

The shell can be a semiconductor material having a composition that is the same as or different from the composition of the core. The shell comprises an overcoat of a semiconductor material on a surface of the core semiconductor nanocrystal can include a Group IV element, a Group II-VI compound, a Group II-V compound, a Group III-VI compound, a Group III-V compound, a Group IV-VI compound, a Group I-III-VI compound, a Group II-IV-VI compound, a Group II-IV-V compound, alloys including any of the foregoing, and/or mixtures including any of the foregoing, including ternary and quaternary mixtures or alloys. Examples include, but are not limited to, ZnO, ZnS, ZnSe, ZnTe, CdO, CdS, CdSe, CdTe, MgS, MgSe, GaAs, GaN, GaP, GaSe, GaSb, HgO, HgS, HgSe, HgTe, InAs, InN, InP, InSb, AlAs, AlN, AlP, AlSb, TlN, TlP, TlAs, TlSb, PbO, PbS, PbSe, PbTe, Ge, Si, an alloy including any of the foregoing, and/or a mixture including any of the foregoing. For example, ZnS, ZnSe or CdS overcoatings can be grown on CdSe or CdTe semiconductor nanocrystals.

Examples of semiconductor nanocrystal (core)shell materials include, without limitation: red (e.g., (CdSe)ZnS (core) shell), green (e.g., (CdZnSe)CdZnS (core)shell, etc.), and blue (e.g., (CdS)CdZnS (core)shell (see further also above for examples of specific light converter nanoparticles, based on semiconductors.

Therefore, in a specific embodiment, the light converter nanoparticles are selected from the group consisting of core-shell nano particles, with the cores and shells comprising one or more of CdS, CdSe, CdTe, ZnS, ZnSe, ZnTe, HgS, HgSe, HgTe, CdSeS, CdSeTe, CdالسTe, ZnSeS, ZnSeTe, ZnSTe, HgSeS, HgSeTe, HgSTe, CdZnS, CdZnSe, CdZnTe, CdHgS, CdHgSe, CdHgTe, HgZnS, HgZnSe, HgZnTe, CdZnSeS, CdZnSeTe, CdZnSTe, CdHgSeS, CdHgSeTe, CdHgSTe, HgZnSeS, HgZnSeTe, HgZnSTe, GaN, GaP, GaAs, AlN, AlP, AlAs, InN, InP, InAs, GaNP, GaNAs, GaPAs, AlNP, AlNAs, AlPAs, InNP, InNAs, InPAs, GaAlNP, GaAlNAs, GaAlPAs, GaInNP, GaInNAs, GaInPAs, InAlNP, InAlNAs, and InAlPAs.

In general, the cores and shells comprise the same class of material, but essentially consist of different materials, like a ZnS shell surrounding a CdSe core, etc.

Additionally or alternatively, the further luminescent material may also comprise other luminescent materials, such as one or more of selected from the group consisting of divalent europium containing nitride luminescent material or a divalent europium containing oxonitride luminescent material, such as one or more materials selected from the group consisting of (Ba,Sr,Ca)S:Eu, (Mg,Sr,Ca)AlSiN$_3$:Eu and (Ba,Sr,Ca)$_2$Si$_5$N$_8$:Eu. In these compounds, europium (Eu) is substantially or only divalent, and replaces one or more of the indicated divalent cations. In general, Eu will not be present in amounts larger than 10% of the cation, especially in the range of about 0.5-10%, more especially in the range of about 0.5-5% relative to the cation(s) it replaces. The term ":Eu" or ":Eu$^{2+}$", indicates that part of the metal ions is replaced by Eu (in these examples by Eu$^{2+}$). For instance, assuming 2% Eu in CaAlSiN$_3$:Eu, the correct formula could be (Ca$_{0.98}$Eu$_{0.02}$)AlSiN$_3$. Divalent europium will in general replace divalent cations, such as the above divalent alkaline earth cations, especially Ca, Sr or Ba. The material (Ba,Sr,Ca)S:Eu can also be indicated as MS:Eu, wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Further, the material (Ba,Sr,Ca)$_2$Si$_5$N$_8$:Eu can also be indicated as M$_2$Si$_5$N$_8$:Eu, wherein M is one or more elements selected from the group consisting of barium (Ba), strontium (Sr) and calcium (Ca); especially, M comprises in this compound Sr and/or Ba. In a further specific embodiment, M consists of Sr and/or Ba (not taking into account the presence of Eu), especially 50-100%, especially 50-90% Ba and 50-0%, especially 50-10% Sr, such as Ba$_{1.5}$Sr$_{0.5}$Si$_5$N$_8$:Eu, (i.e. 75% Ba; 25% Sr). Here, Eu is introduced and replaces at least part of M i.e. one or more of Ba, Sr, and Ca). Likewise, the material (Ba,Sr,Ca)AlSiN$_3$:Eu can also be indicated as MAlSiN$_3$:Eu wherein M is one or more elements selected from the group consisting of barium (Ba), strontium (Sr) and calcium (Ca); especially, M comprises in this compound calcium or strontium, or calcium and strontium, more especially calcium. Here, Eu is introduced and replaces at least part of M (i.e. one or more of Ba, Sr, and Ca). Preferably, in an embodiment the further luminescent material comprises (Ca,Sr,Mg)AlSiN$_3$:Eu, preferably CaAlSiN$_3$:Eu. Further, in another embodiment, which may be combined with the former, the further luminescent material comprises (Ca,Sr,Ba)$_2$Si$_5$N$_8$:Eu, preferably (Sr,Ba)$_2$Si$_5$N$_8$:Eu. The terms "(Ca,Sr,Ba)" indicate that the corresponding cation may be occupied by calcium, strontium or barium. It also indicates that in such material corresponding cation sites may be occupied with cations selected from the group consisting of calcium, strontium and barium. Thus, the material may for instance comprise calcium and strontium, or only strontium, etc.

The further luminescent material may also comprise one or more luminescent materials selected from the group consisting of a trivalent cerium containing garnet (see above) and a trivalent cerium containing oxonitride. The oxonitride materials are in the art often also indicated as oxynitride materials.

Hence, in an embodiment the further luminescent material is configured to provide at least red light, the organic luminescent material is configured to provide at least green and/or yellow light, and especially the light source is configured to provide blue light. As indicated the further luminescent material comprises a quantum dot based luminescent material.

Hence, in an embodiment the light source is configured to provide blue light, the lighting device further comprises a further luminescent material configured to provide red light, wherein the further luminescent material comprises a luminescent material selected from the group consisting of (Ba,Sr,Ca)S:Eu, (Mg,Sr,Ca)AlSiN$_3$:Eu and (Ba,Sr,Ca)$_2$Si$_5$N$_8$:Eu (and optionally a quantum dot based luminescent material (see also above))(and optionally an organic red luminescent (see also below)). Alternatively or additionally, the further luminescent material comprises a quantum dot based luminescent material. The further luminescent material may be embedded in the matrix and/or may be applied as coating to the matrix. Additionally or alternatively, the further luminescent material may also be arranged elsewhere in the lighting device, but may still be configured to convert at least part of the light source light into visible light, that may optionally complement the light of the organic luminescent material. Hence, in a specific embodiment the lighting device further comprises a quantum dot based luminescent material embedded in the matrix.

In yet another embodiment, the further luminescent material comprises an organic luminescent materials, especially an organic red luminescent material. In a further specific embodiment, the further luminescent material comprises an organic luminescent material as defined by formula (II):

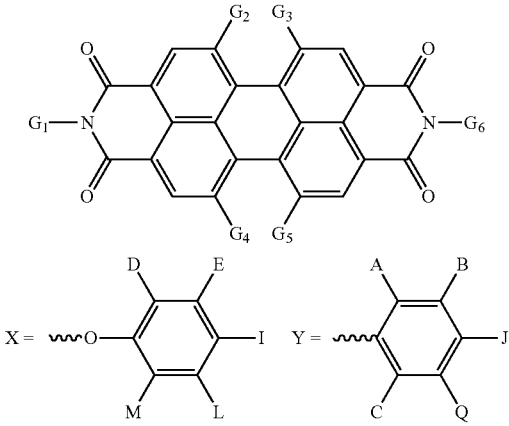

in which:
G$_1$ and G$_6$ independently comprise a group selected from a linear alkyl, a branched alkyl, an oxygen-containing alkyl, a cycloalkyl, a naphtyl, and Y;
  wherein each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms;
G$_2$, G$_3$, G$_4$ and G$_5$ independently comprise a group selected from hydrogen, fluorine, chorine, isopropyl, t-butyl, methoxy, alkyl with up to 16 carbon atoms, and oxygen-containing alkyl with up to 16 carbon atoms, and X;
  wherein each of D, E, I, L and M independently comprise a group selected from hydrogen, fluorine, chlorine, isopropyl, t-butyl, methoxy, alkyl with up to 16 carbon atoms, and an oxygen-containing alkyl with up to 16 carbon atoms;
and in which
at least two selected from G$_2$, G$_3$, G$_4$, and G$_5$ at least comprise X, wherein independently at least one of D, E, I, L and M of at least two of said at least two selected from G$_2$, G$_3$, G$_4$, and G$_5$ comprise a group selected from fluorine and chlorine, especially fluorine.

The above described organic luminescent material of formula II is of the perylene type. Perylenes are known in the art and are for instance described in U.S. Pat. No. 4,845,223, US 2003/0111649, WO 2010/116294 (incorporated herein by reference), and WO 2012/113884.

The term "further luminescent material" may thus also relate to a plurality of different further luminescent materials. The further luminescent material may be comprised by the light converter, such as embedded in the matrix, like especially the organic luminescent material, or may be outside the light converter, such as a layer on the light converter, or may be elsewhere in the lighting device. Combinations of two or more of such configurations are also possible. Hence, in an embodiment the further luminescent material, such as the quantum dot based luminescent material, is embedded in the matrix.

As indicated above, the lighting device comprises (a) a light source configured to generate light source light, and (b) a light converter configured to convert at least part of the light source light into visible converter light.

The light converter, or especially the luminescent material, is configured to convert at least part of the light source light. In order words, one may say that the light source is radiationally coupled to the light converter, especially the luminescent material. When the light source comprises a substantially UV light emitting light source, the luminescent material may be configured to convert substantially all light source light that impinges on the luminescent material. In case the light source is configure to generate blue light, the luminescent material may partly convert the light source light. Dependent upon the configuration, a part of the remaining light source light may be transmitted through a layer comprising the luminescent material. Here, the term may relate to one or more of the organic luminescent material and the further luminescent material.

The term light source may in principle relate to any light source known in the art, but may especially refers to a LED-based light source, herein further indicated as LED. The description below will—for the sake of understanding—only addresses LED-based light sources. The light source is configured to provide UV and/or blue light. In a preferred embodiment, the light emitting diode is configured to generate LED light with a blue component. In other words, the light source comprises a blue LED. Hence, in an embodiment, the light source is configured to generate blue light. Especially, the LED is a solid state LED.

In yet another embodiment, the light emitting diode is configured to generate LED light with a UV component. In other words, the light source comprises a UV LED. When a UV light source is applied and blue or white light is desired, as blue component, for instance the well-known materials BaMgAl$_{10}$O$_{17}$:Eu$^{2+}$ and/or (Sr,Ba,Ca)$_5$(PO$_4$)$_3$Cl:Eu$^{2+}$ may be applied. However, also other luminescent materials that are able to convert UV light into blue light may alternatively or additionally be applied. Such blue luminescent material may be applied as part of the light source, or remote, and may optionally (also) be comprised by the light converter. All luminescent materials described herein may be radiationally coupled with the light source, though optionally one or more luminescent materials are radiationally coupled with one or more other luminescent materials (i.e. they are configured to receive mission light of those one or more other luminescent materials, and can get be excited by that emission light).

Preferably, the light source is a light source that during operation emits at least light at a wavelength selected from the range of 200-490 nm, especially a light source that during operation emits at least light at wavelength selected from the range of 400-490 nm, even more especially in the range of 440-490 nm. This light may partially be used by the luminescent material(s) (see below). In a specific embodiment, the light source comprises a solid state LED light source (such as a LED or laser diode). The term "light source" may also relate to a plurality of light sources, such as 2-20 (solid state) LED light sources. Hence, the term LED may also refer to a plurality of LEDs. Hence, in a specific embodiment, the light source is configured to generate blue light. In a further embodiment, the lighting device might be applied as back lighting unit in an LCD application. Hence, the invention provides in a further aspect a liquid crystal display device comprising a back lighting unit, wherein the back lighting unit comprises one or more lighting devices as defined herein.

The term white light herein, is known to the person skilled in the art. It especially relates to light having a correlated color temperature (CCT) between about 2000 and 20000 K, especially 2700-20000 K, for general lighting especially in the range of about 2700 K and 6500 K, and for backlighting purposes especially in the range of about 7000 K and 20000

K, and especially within about 15 SDCM (standard deviation of color matching) from the BBL (black body locus), especially within about 10 SDCM from the BBL, even more especially within about 5 SDCM from the BBL.

In an embodiment, the light source may also provide light source light having a correlated color temperature (CCT) between about 5000 and 20000 K, e.g. direct phosphor converted LEDs (blue light emitting diode with thin layer of phosphor for e.g. obtaining of 10000 K). Hence, in a specific embodiment the light source is configured to provide light source light with a correlated color temperature in the range of 5000-20000 K, even more especially in the range of 6000-20000 K, such as 8000-20000 K. An advantage of the relative high color temperature may be that there may be a relative high blue component in the light source light.

The lighting device comprises at least the light converter comprising the organic luminescent material according to formula I. Other (further) luminescent materials, may also be present. The one or more further luminescent materials may each individually be comprised by the matrix but may also be provides as coating or layer on the matrix, or may be arranged elsewhere in the lighting device.

The lighting device may especially be configured to be able to provide white light. Optionally, the lighting device is configured to provide colored light or is configured to be able to provide color light and white light, depending upon how the lighting device is controlled.

The terms "violet light" or "violet emission" especially relates to light having a wavelength in the range of about 380-440 nm. The terms "blue light" or "blue emission" especially relates to light having a wavelength in the range of about 440-490 nm (including some violet and cyan hues). The terms "green light" or "green emission" especially relate to light having a wavelength in the range of about 490-560 nm. The terms "yellow light" or "yellow emission" especially relate to light having a wavelength in the range of about 540-570 nm. The terms "orange light" or "orange emission" especially relate to light having a wavelength in the range of about 570-600. The terms "red light" or "red emission" especially relate to light having a wavelength in the range of about 600-750 nm. The term "pink light" or "pink emission" refers to light having a blue and a red component. The terms "visible", "visible light" or "visible emission" refer to light having a wavelength in the range of about 380-750 nm.

The light source may be configured in a chamber, with reflective wall(s) (such as coated with a reflective material like $TiO_2$), and a light transmissive window. In an embodiment, the window is the light conversion layer. In yet a further embodiment, the window comprises the light conversion layer. This layer may be arranged upstream of the window or downstream of the window. In yet a further embodiment, light conversion layers are applied at both sides of the window.

The terms "upstream" and "downstream" relate to an arrangement of items or features relative to the propagation of the light from a light generating means (here the especially the first light source), wherein relative to a first position within a beam of light from the light generating means, a second position in the beam of light closer to the light generating means is "upstream", and a third position within the beam of light further away from the light generating means is "downstream".

It may be advantageous, in view of efficiency and/or stability, to arrange the light converter (and optionally also other luminescent material(s) not within the light converter), at a non-zero distance, such as 0.5-50 mm, like 1-50 mm, from the light source. Hence, in an embodiment, the light converter may be configured at a non-zero distance of the light source. For instance, the light converter, or especially the (organic) luminescent material(s), may be applied to or may be comprised by a window of the lighting unit. Hence, in an embodiment, the light converter is configured at a non-zero distance from the light source. Note however that the invention is not limited to applications wherein the distance between the light converter and the light source is non-zero. The invention, and the herein described specific embodiments, may be also applied in other embodiments wherein the light source and light converter are in physical contact. In such instances, the light converter may especially be configured in physical contact with e.g. a LED die.

In case the light source is configured to provide blue light, the luminescent material may be configured to convert only part of the light source light. In an embodiment, the blue light of the light source and the light of the organic luminescent material light and the light of the optional further luminescent material, such as a nano particles based luminescent material, together may in an embodiment provide white light.

The term "substantially" herein, such as in "substantially all emission" or in "substantially consists", will be understood by the person skilled in the art. The term "substantially" may also include embodiments with "entirely", "completely", "all", etc. Hence, in embodiments the adjective substantially may also be removed. Where applicable, the term "substantially" may also relate to 90% or higher, such as 95% or higher, especially 99% or higher, even more especially 99.5% or higher, including 100%. The term "comprise" includes also embodiments wherein the term "comprises" means "consists of". The term "and/or" especially relates to one or more of the items mentioned before and after "and/or". For instance, a phrase "item 1 and/or item 2" and similar phrases may relate to one or more of item 1 and item 2. The term "comprising" may in an embodiment refer to "consisting of" but may in another embodiment also refer to "containing at least the defined species and optionally one or more other species".

Furthermore, the terms first, second, third and the like in the description and in the claims, are used for distinguishing between similar elements and not necessarily for describing a sequential or chronological order. It is to be understood that the terms so used are interchangeable under appropriate circumstances and that the embodiments of the invention described herein are capable of operation in other sequences than described or illustrated herein.

The devices herein are amongst others described during operation. As will be clear to the person skilled in the art, the invention is not limited to methods of operation or devices in operation.

It should be noted that the above-mentioned embodiments illustrate rather than limit the invention, and that those skilled in the art will be able to design many alternative embodiments without departing from the scope of the appended claims. In the claims, any reference signs placed between parentheses shall not be construed as limiting the claim. Use of the verb "to comprise" and its conjugations does not exclude the presence of elements or steps other than those stated in a claim. The article "a" or "an" preceding an element does not exclude the presence of a plurality of such elements. The mere fact that certain measures are recited in mutually different dependent claims does not indicate that a combination of these measures cannot be used to advantage.

The invention further applies to a device comprising one or more of the characterizing features described in the description and/or shown in the attached drawings. The invention further pertains to a method or process comprising one or more of the characterizing features described in the description and/or shown in the attached drawings.

The various aspects discussed in this patent can be combined in order to provide additional advantages. Furthermore, some of the features can form the basis for one or more divisional applications.

In yet a further embodiment, the invention provides a lighting device, as described herein, with the organic luminescent material of formula I, and/or a light converter, as described herein, with the organic luminescent material of formula I, and/or the organic luminescent material of formula I, in which A, B, C, J, Q are independently selected from hydrogen, halogen, $R_1$, $OR_2$, $NHR_7$, and $NR_2R_7$, wherein $R_1$ is independently selected from a $C_2$-$C_{18}$ hydrocarbon, an arylgroup containing $C_6$-$C_{24}$ hydrocarbon, and a heteroarylgroup containing $C_6$-$C_{24}$ hydrocarbon; and wherein $R_2$ and $R_7$ are independently selected from a $C_1$-$C_{18}$ hydrocarbon, an arylgroup containing $C_6$-$C_{24}$ hydrocarbon, and a heteroarylgroup containing $C_6$-$C_{24}$ hydrocarbon; and in which $G_2$-$G_9$ are independently selected from hydrogen, halogen, $R_3$, $OR_3$, $NHR_3$, and $NR_4R_3$, wherein $R_3$ and $R_4$ are independently selected from an $C_1$-$C_{18}$ hydrocarbon, an arylgroup containing $C_6$-$C_{24}$ hydrocarbon, and an heteroarylgroup containing $C_6$-$C_{24}$ hydrocarbon, and where applicable, when one or more of $G_2$-$G_9$ are independently selected from $R_3$, $OR_3$, $NHR_3$, and $NR_4R_3$, wherein $R_3$=Y, with D, E, I, L and M independently being selected from hydrogen, halogen, $R_5$, $OR_5$, $NHR_5$, and $NR_6R_5$, wherein $R_5$ and $R_6$ are independently selected from an $C_1$-$C_{18}$ hydrocarbon, an arylgroup containing $C_6$-$C_{24}$ hydrocarbon, and an heteroarylgroup containing $C_6$-$C_{24}$ hydrocarbon. Here, hydrocarbon may relate to a substituted or unsubstituted, to a saturated or unsaturated hydrocarbon, etc. etc. Further, such hydrocarbon may contain cyclic or non-cyclic groups, etc. The phrases "aryl group containing" or "heteroaryl group containing" and similar phrases indicate that such hydrocarbon at least comprises an aryl group or a heteroaryl group, respectively, but may in embodiments also comprise two or more of such groups, respectively.

BRIEF DESCRIPTION OF THE DRAWINGS

Embodiments of the invention will now be described, by way of example only, with reference to the accompanying schematic drawings in which corresponding reference symbols indicate corresponding parts, and in which.

DETAILED DESCRIPTION OF THE EMBODIMENTS

Figure 1A:
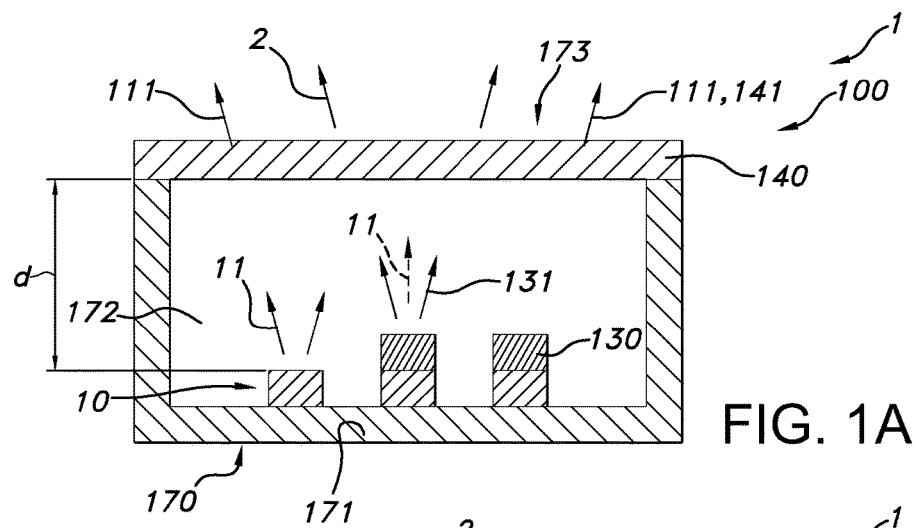
FIGS. 1a-1f schematically depict some embodiments of the lighting device; these drawings are not necessarily on scale.

FIG. 1a schematically depicts a lighting device 1 with a light converter 100, which in this embodiment at least comprises the organic luminescent material 140 according to formula 1. The organic luminescent material 140 is in this embodiment embedded in a (polymeric) matrix, such as PET. As can be seen, a remote version is shown, with a non-zero distance d between the luminescent material (in the light converter 100) and the light source(s), indicated with reference(s) 10. The lighting device 1 comprises one or more light sources 10 which are configured to provide light source light 11, especially blue and/or UV light. The lighting device 1 may comprise a plurality of such light sources. When lighting device light, indicated with reference 2, of a white nature is desired, it may be necessary to us an RGB concept, wherein the green and/or yellow color, or at least part thereof, is provided by the green and/or yellow luminescent material 140, and the blue and red light are provided by one or more of the light source and a combination of the light source and another luminescent material, especially the further luminescent material. The further luminescent material is indicated with reference 130, and provides further luminescent material light 131.

The organic luminescent material 140 according to formula I provides upon excitation by the light source light 11 and/or by emission of one or more other luminescent materials, such as e.g. the further luminescent material light 131, organic luminescent material light 141. Here, the light converter 100 is remote from the light source 10, and the organic luminescent material, which is embedded in the light converter 100, is thus also remote. The optional further luminescent material 130 can also be arranged remote, see below, but is by way of example close to the light source 10, such as in a dome and/or as layer on the LED die.

Just by way of example, one light source has been depicted without the further luminescent material 130. However, in another embodiment, all light sources 10 may be configured with at least further luminescent material 130. Also, by way of example three light sources 10 have been depicted. However, more or less than three light sources may be applied.

Note that the light source 10 may provide blue and/or UV light. The further luminescent material 130 may especially, upon excitation (by said light of the light source 10) provide red light. Optionally, the further luminescent material 130 may also provide green and/or yellow light.

FIG. 1a, and other figures, schematically depict a device with a light chamber 170, with an enclosure 171, at least partly enclosing a cavity 172, which has a transmissive part 173. In an embodiment, the transmissive part 173 comprises the light converter 100, or may especially consist of the light converter 100. The surface of the non-transmissive part of the enclosure is indicated with reference 171. At least part of the surface 171 may comprise a reflector, such as a reflective coating.

The light converter 100 provides upon excitation light converter light 111, which at least comprises organic luminescent material light 141 but may optionally comprise other luminescence light as well (see below). The lighting device light, indicated with reference 2, at least comprises light converter light 111/organic luminescent material light 141, but may optionally comprise one or more of the light source light 11, further luminescent material light 131, and light of other luminescent materials (not depicted).

Figure 1B:
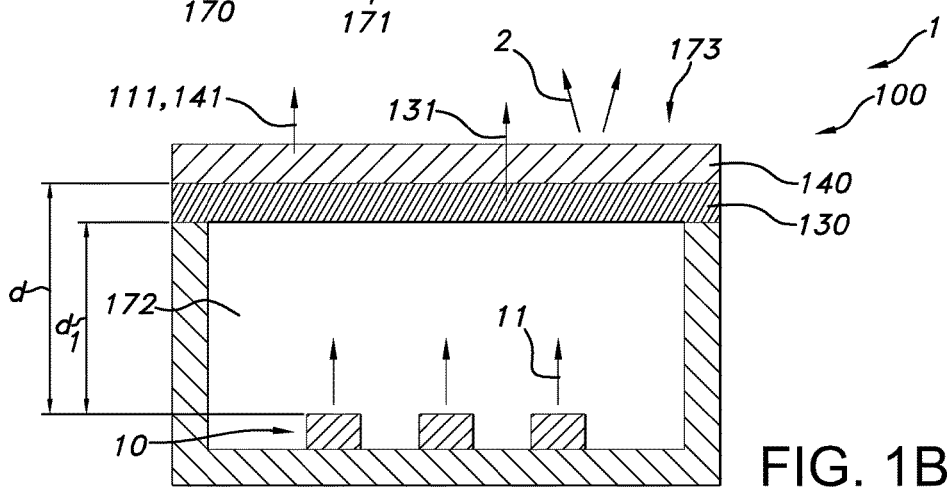

FIG. 1b schematically depicts an embodiment wherein the light converter 100 may comprise an upstream layer with further luminescent material 130. Optionally, this may be a light converter comprising two layers comprising the same matrix, but comprising different luminescent materials. The distance of the layer with further luminescent material 130 to the light source is indicated with dl. This distance is in this embodiment non-zero, in contrast to the embodiment schematically depicted in FIG. 1a.

Figure 1C:
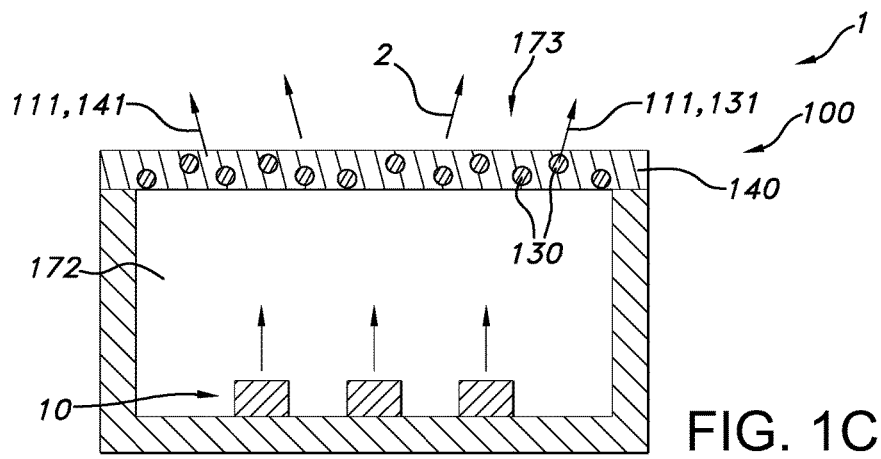

FIG. 1c schematically depicts an embodiment wherein the light converter 100 comprises the further luminescent material 140, e.g. in the form of quantum dots, and the organic luminescent material 130 according to formula I. Both the organic luminescent material 140 and the further luminescent material 130 are in this embodiment embedded in the (remote) light converter, i.e. embedded in the (polymeric) matrix of the light converter 100.

Figure 1D:
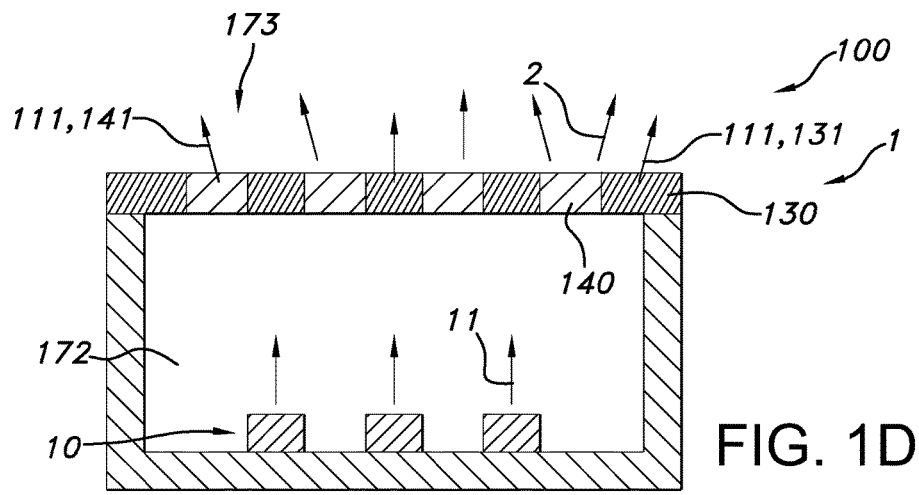

FIG. 1d schematically depicts an embodiment wherein the transmissive part 173 comprises at least two types of segments, with volumes over 0.25 cm$^3$, wherein the two types of segments comprise different weight ratios organic luminescent material and further luminescent material. For instance, first segments only comprise the organic luminescent material 140 as luminescent material and second segments only comprises further luminescent material 130 as luminescent material. The organic luminescent material 140 may also in this embodiment be embedded in a (polymeric) matrix, such as PET. Likewise, also the further luminescent material 130 may be embedded in a (polymeric) matrix, such as PET.

Figure 1E:
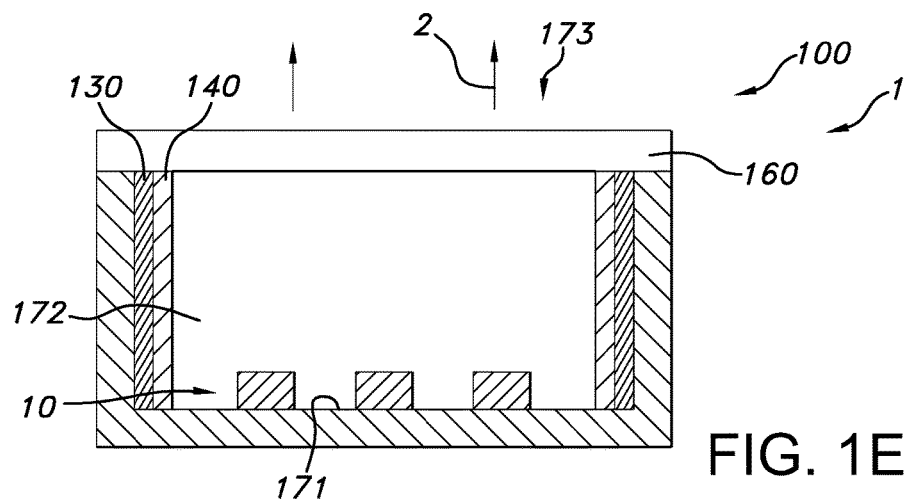

FIG. 1e schematically depicts an embodiment wherein the enclosure 170 comprises a transmissive diffuser 160 (as transmissive part 173) and the light converter is applied to at least part of the non-transmissive part of the enclosure 171.

Figure 1F:
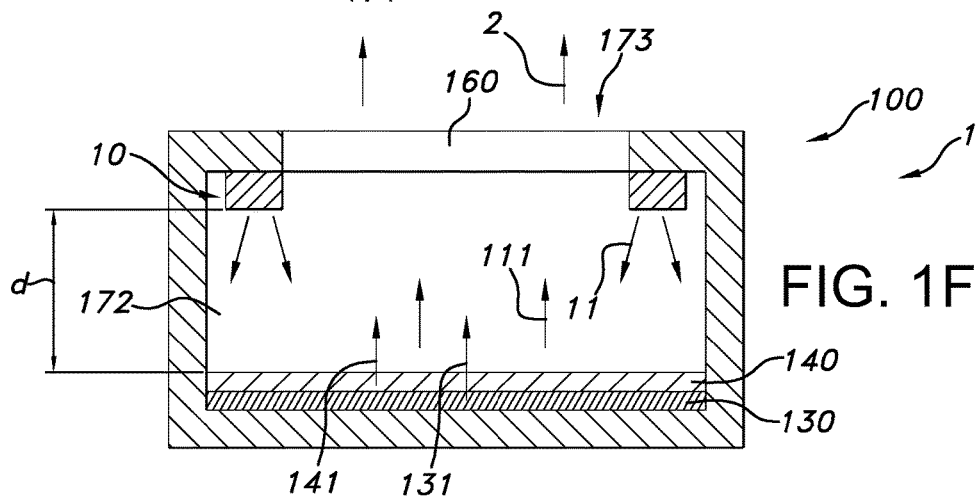

FIG. 1f schematically depicts a reflective configuration. As mentioned above, the organic luminescent material 140 and optionally the further luminescent material 140 may (both) be embedded in a (polymeric) matrix.

Combinations of embodiments may also be applied, like the segmented light converter of FIG. 1d in combination with or alternative to the light converter(s) shown in the other drawings, such as e.g. 1a, 1b, 1e, 1f.

In FIGS. 1a-1d, the lighting device comprises a light transmissive window, which comprises or consists of the matrix. Hence, the matrix may be applied as light transmissive window. In FIGS. 1e-1f, a transmissive diffuser is used as transmissive window. The transmissive window is used as an envelope, or as part of an envelope. Here, the transmissive window envelopes at least part of the cavity 172. Note that the transmissive window is not necessarily flat. The transmissive window, comprising in embodiments the matrix, may also be curved, like in the embodiment of a TLED or in a retrofit incandescent lamp (bulb).

EXAMPLES

Figure 2A:
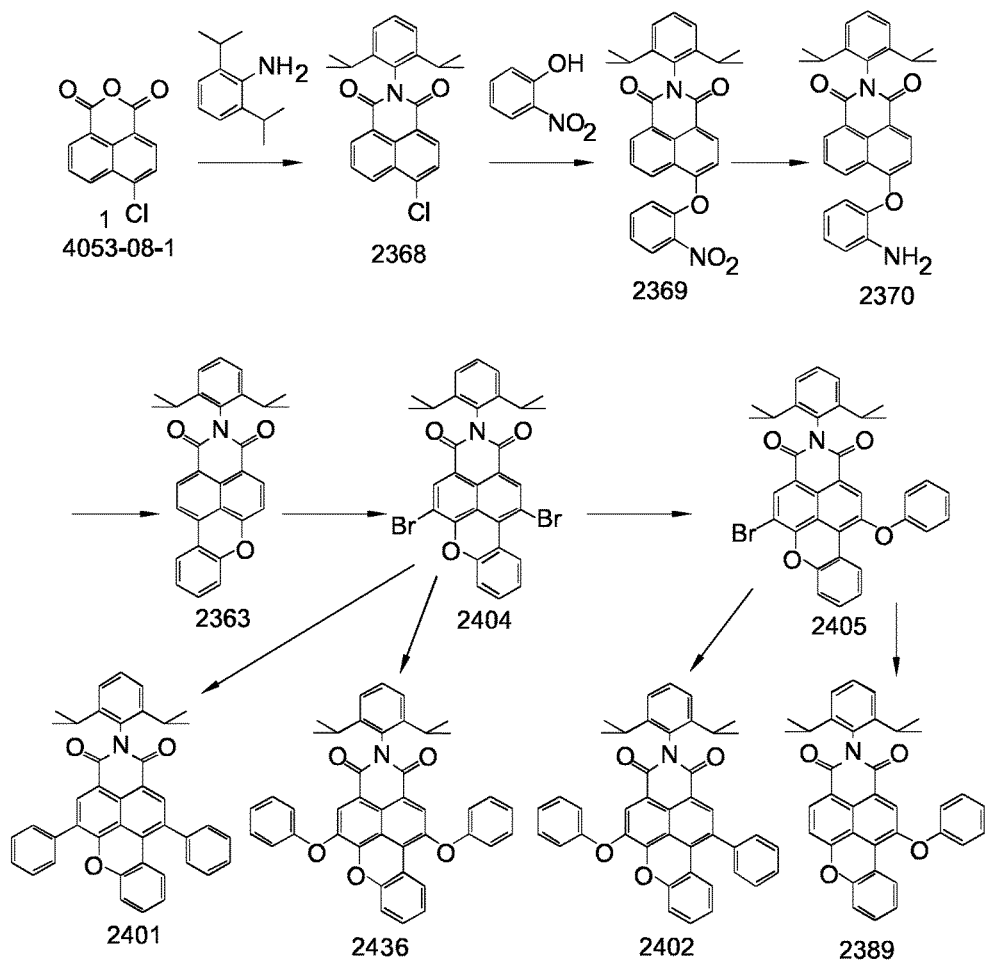
FIGS. 2a-2c show synthesis schemes and a number of organic luminescent materials made, respectively.
Figure 2B:
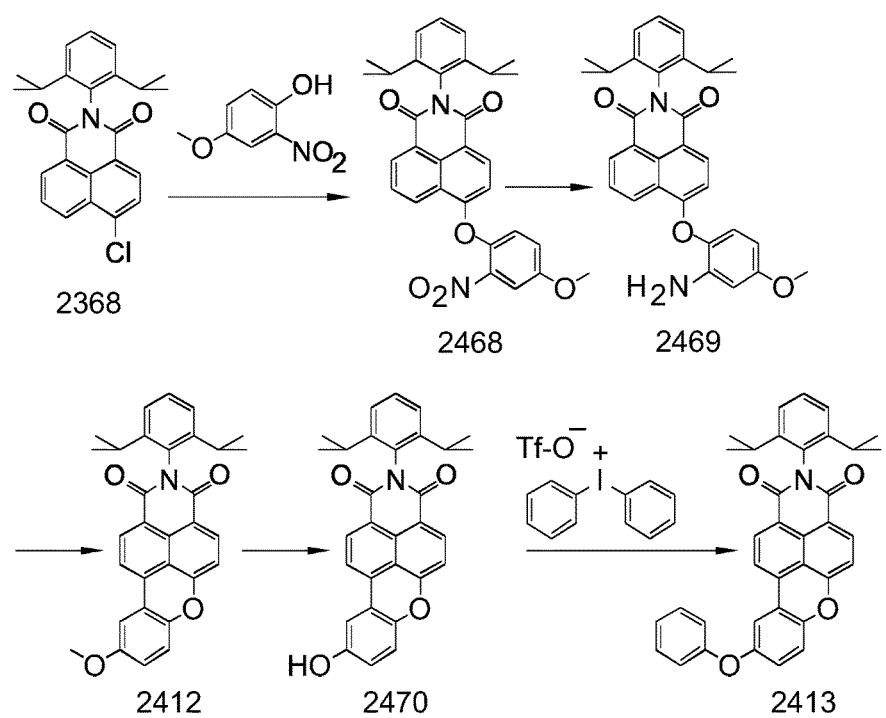
Figure 2C:
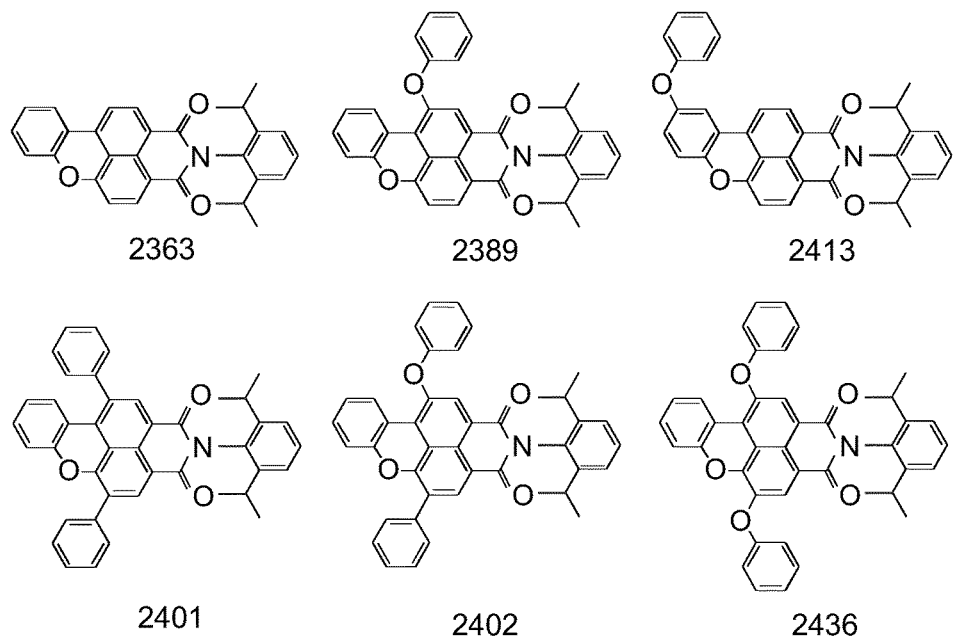
Figure 3:
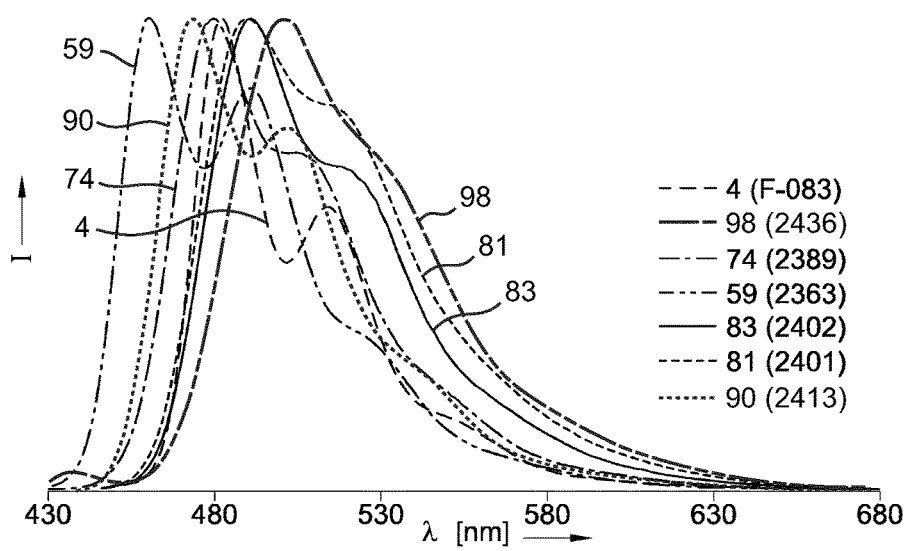
FIG. 3 shows luminescence spectra (at RT) in ethyl acetate of those materials, also in comparison with F083 (perylene)

By way of Example, a few syntheses are described below. Two synthesis schemes are depicted in FIGS. 2a and 2b, respectively; a number of organic luminescent materials made is schematically depicted in FIG. 2c. Luminescence spectra of those materials, also in comparison with F083 (prior art system), are depicted in FIG. 3.

Synthesis of 2363

1. 6-chloro-2-(2,6-diisopropylphenyl)-1H-benzo[de]isoquinoline-1,3(2H)-dione (2368)

A mixture of 4-chloronaphthalic anhydride (10 g, 43.0 mmol) and 2,6-diisopropylaniline (16.2 mL, 86 mmol) in AcOH (300 mL) was refluxed overnight. The mixture was cooled and poured into water. The precipitate was collected by filtration, washed with water and dried under vacuum. Purification by column chromatography on SiO$_2$ (dichloromethane/heptane=2:1) gave 7.5 g (44%) of pure compound 2368.

2. 4-(2-nitrophenoxy)-N-(2,6-diisopropylphenyl)-1,8-naphthalimide (2369)

A mixture of 2368 (7.5 g, 19.1 mmol), 2-nitrophenol (13.5 g, 34.4 mmol) and K$_2$CO$_3$ (5.3 g, 38.2 mmol) in NMP (300 mL) was stirred at 90° C. under nitrogen overnight. The mixture was cooled and poured into a mixture of AcOH (150 mL) and ice-water. After 5 minutes, 2 N HCl (200 mL) was added and the mixture was extracted with toluene (4×). the combined organic layers were washed with water and brine, dried (Na$_2$SO$_4$), filtered and concentrated. Purification by column chromatography on SiO$_2$ (dichloromethane/heptane=1/1 to 2:1) gave 6.7 g (71%) of pure compound 2369 as a white solid.

3. 4-(2-aminophenoxy)-N-(2,6-diisopropylphenyl)-1,8-naphthalimide (2370)

A solution of compound 2369 (5.7 g, 11.5 mmol) in a mixture of THF (60 mL) and MeOH (50 mL) under nitrogen atmosphere was warmed to get a clear solution. The mixture was then cooled to room temperature and 10% Pd/C (2 g) was added. The mixture was stirred 2 h at room temperature under hydrogen atmosphere (balloon) then filtered over a pad of celite and concentrated. Purification by column chromatography on SiO$_2$ (dichloromethane) gave 4.9 g (90%) of pure compound 2370 as a yellow solid.

4. 2-(2,6-diisopropylphenyl)-1H-xantheno[2,1,9-def]isoquinoline-1,3(2H)-dione (2363)

A solution of compound 2370 (5.1 g, 11.0 mmol) in AcOH (80 mL) was treated with hydrochloric acid (1.5 M, 21 mL) and sodium nitrite (3.0 g, 43.9 mmol in 20 mL water) at 0° C. After 60 minutes, a solution of CuSO$_4$.5H$_2$O (11.24 g, 45.0 mmol) in water (130 mL) was added. The mixture was refluxed for another 0.5 h and then allowed to cool. The precipitated yellow solid was filtered, washed with water and dried under vacuum. Purification by column chromatography on SiO$_2$ (dichloromethane/heptane=1/1 to 2:1) gave 850 mg (17%) of pure compound 2363 as a yellow solid. M+H=448.1. $\lambda_{max}$ (ethyl acetate)=421 nm, $\epsilon$=25500 and 444 nm $\epsilon$=21300. $\lambda$(em) (ethyl acetate) 460 nm and 490 nm.

Synthesis of 2389

1. 5,11-dibromo-2-(2,6-diisopropylphenyl)-1H-xantheno[2,1,9-def]isoquinoline-1,3(2H)-dione (2404)

Bromine (2.7 mL, 53.64 mmol) was added to a solution compound 2363 (2 g, 4.47 mmol) in CHCl$_3$ (160 mL) under nitrogen. The mixture was stirred at 60° C. for 5 h cooled to room temperature and concentrated. The various brominates products were separated by column chromatography (SiO$_2$, eluent:toluene dichloromethane 1/1 to 2/1). Compound 2404 (1.8 g, 66%) was obtained as a yellow solid.

2. 2-(2,6-diisopropylphenyl)-5-bromo-11-phenoxy-1H-xantheno[2,1,9-def]isoquinoline-1,3(2H)-dione (2405)

A mixture of 2404 (1.4 g, 2.31 mmol), phenol (1.2 g, 12.75 mmol) and K$_2$CO$_3$ (2.2 g, 15.92 mmol) in NMP (60 mL) was stirred at 90° C. under nitrogen overnight. Then, the contents of the flask were poured into a cold 20% acetic acid solution in water. After 5 minutes, 2 N aqueous HCl was added and stirred for 10 minutes and the precipitated solid was filtered, washed neutral with warm water and vacuum dried at 60° C. The residue was coated on silica gel and purified by column chromatography (SiO$_2$, eluent:dichloromethane/Heptane 1/1 to 2/1). Compound 2405 (1.1 g, 76%) was obtained as a yellow solid.

3. 2-(2,6-diisopropylphenyl)-11-phenoxy-1H-xantheno[2,1,9-def]isoquinoline-1,3(2H)-dione (2389)

To a clear solution of compound 2405 (600 mg, 0.97 mmol) in THF (80 mL) and MeOH (10 mL) under nitrogen was added 10% Pd/C (100 mg) and the reaction was placed under hydrogen atmosphere with a balloon. The mixture was stirred at 30° C. overnight and then filtered over Celite. The crude solid was purified by column chromatography (SiO$_2$, eluent: toluene/dichloromethane 3/2). Compound 2389 (540 mg, 98%) was obtained as a yellow solid. M+H=540.2. $\lambda_{max}$ (ethyl acetate)=428 nm, $\epsilon$=19300 and 449 nm, $\epsilon$=18500. $\lambda$(em) (ethyl acetate) 479 nm and 506 nm.

Synthesis of 2-(2,6-diisopropylphenyl)-5,11-diphenyl-1H-xantheno[2,1,9-def]isoquinoline-1,3(2H)-dione (2401)

Compound 2404 (500 mg, 0.83 mmol), phenylboronic acid (810 mg, 6.64 mmol), Pd(PPh$_3$)$_4$ (40 mg, 0.03 mmol) and Na$_2$CO$_3$ (265 mg, 2.50 mmol) were added to a degassed mixture of EtOH (1 mL), benzene (15 mL) and water (2 mL) under nitrogen. The mixture was reacted at 80° C. overnight. The reaction was quenched by addition of water and extracted with dichloromethane (3×). the combined organic layer was washed with water, brine, dried (Na$_2$SO$_4$), filtered and concentrated under reduced pressure. The crude solid was purified by column chromatography (SiO$_2$, eluent: DCM/heptane 2/1). Compound 2401 (490 mg, 98%) was obtained as a yellow solid. M+H=600.3. $\lambda_{max}$ (ethyl acetate)=435 nm, $\epsilon$=17700 and 455 nm, $\epsilon$ 15600. $\lambda$(em) (ethyl acetate) 489 nm and 516 nm.

Synthesis of 2-(2,6-diisopropylphenyl)-11-phenoxy-5-phenyl-1H-xantheno[2,1,9-def]isoquinoline-1,3 (2H)-dione (2402)

Compound 2405 (400 mg, 0.65 mmol), phenylboronic acid (396 mg, 3.25 mmol), Pd(PPh$_3$)$_4$ (40 mg, 0.03 mmol) and Na$_2$CO$_3$ (130 mg, 1.22 mmol) were added to a degassed mixture of EtOH (1 mL), benzene (15 mL) and water (2 mL) under nitrogen. The mixture was reacted at 80° C. overnight under nitrogen. The reaction was quenched by addition of water and extracted with dichloromethane (3×). the combined organic layer was washed with water, brine, dried (Na$_2$SO$_4$), filtered and concentrated under reduced pressure. The crude solid was purified by column chromatography (SiO$_2$, eluent:dichloromethane/heptane 1/1 to 3/2). Compound 2402 (390 mg, 97%) was obtained as a yellow solid. M+H=616.0. $\lambda_{max}$ (ethyl acetate)=436 nm, $\epsilon$=17500 and 457 nm, $\epsilon$=16700. $\lambda$(em) (ethyl acetate) 491 nm and 521 nm.

Synthesis of 2413

1. 2-(2,6-diisopropylphenyl)-6-(4-methoxy-2-nitrophenoxy)-1H-benzo[de]isoquinoline-1,3(2H)-dione (2468)

A mixture of 2368 (12.0 g, 30.62 mmol), 4-methoxy-2-nitrophenol (8.9 g, 52.86 mmol) and K$_2$CO$_3$ (8.1 g, 58.60 mmol) in N-methylpyrolidone (150 mL) was stirred at 90° C. under nitrogen overnight. The mixture was cooled and poured into a mixture of acetic acid and ice-water. After 5 minutes, 2 N HCl was added and the precipitate was collected by filtration, washed with water and with methanol (removed excess of phenol) and dried under vacuum to give compound 2468 (14 g, 87% yield) as a solid.

2. 4-(4-Methoxy-2-aminophenoxy)-N-(2,6-diisopropylphenyl)-1,8-naphthalimide 2469

To a solution of compound 2468 (14.0 g, 28.31 mmol) in a mixture of THF (130 mL) and methanol (60 mL) under nitrogen atmosphere was added 10% Pd/C (3 g). The mixture was stirred overnight at room temperature under hydrogen atmosphere (balloon) then filtered over a pad of celite and concentrated. To give compound 2469 (14 g, quantitative yield) as a yellow solid.

3. 2-(2,6-diisopropylphenyl)-9-methoxy-1H-xantheno[2,1,9-def]isoquinoline-1,3(2H)-dione 7 (2412)

A nitrosylsulfuric acid solution (40 wt. % nitric acid in sulphuric acid, 5.8 mL, 33.96 mmol) was added dropwise to a solution of compound 2469 (14.0 g, 28.3 mmol) in a mixture of acetic acid (100 mL) and propionic acid (30 mL) at 0-5° C. After 1 h, the diazonium liquor was added portionwise to a boiling solution of hydrated copper (II) sulphate (28.3 g, 113.2 mmol) in water (250 mL) and acetic acid (16 mL). After the addition was complete, the liquor was boiled for 1 h, cooled, diluted with water and the precipitated yellow solid was filtered, washed with water and dried under vacuum. Purification by column chromatography on SiO$_2$ (dichloromethane/heptane=1/1 to 2:1) gave compound 2412 (1.3 g, 9.6%) as a yellow solid.

4. 2-(2,6-diisopropylphenyl)-9-hydroxy-1H-xantheno[2,1,9-def]isoquinoline-1,3(2H)-dione 2470

A solution of BBr$_3$ (1M in dichloromethane, 2.6 mL, 2.60 mmol) was added to a solution of compound 2412 (350 mg, 0.72 mmol) in dichloromethane (35 mL) at 0° C. under nitrogen. The mixture was stirred at 40° C. overnight, cooled to 0° C. and a solution of NaHCO$_3$ was added. The mixture was extracted with dichloromethane (1×) and then with ethyl acetate (3×) and the combined organic layers were washed with water and brine, dried (Na$_2$SO$_4$), filtered and concentrated. Purification by column chromatography on SiO$_2$ (dichloromethane/methanol=60/1 to 40/1) gave pure compound 2470 (284 mg, 84% yield) as a yellow solid.

5. 2-(2,6-diisopropylphenyl)-9-phenoxy-1H-xantheno[2,1,9-def]isoquinoline-1,3(2H)-dione 2413

Potassium t-butoxide (91 mg, 0.81 mmol) was added to a solution of compound 2470 (342 mg, 0.74 mmol) in THF (50 mL) at 0° C. under nitrogen and the reaction was stirred at this temperature for 15 minutes. diphenyliodonium trifluoromethanesulfonate (473 mg, 1.10 mmol) was added in one portion and the cold bath was removed. The mixture was stirred at 40° C. for 1 h then cooled to 0° C., diluted with dichloromethane and water was added. The organic phase was separated and the water phase was extracted with ethyl acetate (2×). The combined organic phases were washed with brine, dried (Na$_2$SO$_4$), filtered and concentrated. Purification by column chromatography on SiO$_2$ (dichloromethane/heptane=2/1 to 4/1) gave pure compound 2413 (295 mg, 73% yield) as a yellow solid. M+H=540.2. $\lambda_{max}$ (ethyl acetate)=429 nm, $\epsilon$=24800 and 452 nm, $\epsilon$=22100. $\lambda$(em) (ethyl acetate) 473 nm and 501 nm.

Synthesis of 2-(2,6-diisopropylphenyl)-5,11-diphenoxy-1H-xantheno[2,1,9-def]isoquinoline-1,3(2H)-dione (2436)

A mixture of 2404 (2.0 g, 3.3 mmol), phenol (10.0 g, 16.5 mmol) and $Cs_2CO_3$ (6.4 g, 19.8 mmol) in degased 1,4-dioxane (1560 mL) was stirred at 90° C. under nitrogen for 1 h. Then, a mixture of Cu(I)I (314 mg, 1.65 mmol) and N,N-dimethylglycine (510 mg, 495 mmol) in 1,4-dioxane (4 mL) was added and the reaction mixture was stirred at 90° C. under nitrogen overnight. The mixture was cooled to room temperature and the solvent removed under reduced pressure. The residue was dissolved in dichloromethane and SiO2 was added. The dichloromethane was removed under reduced pressure and the product coated on silica was poured on top of a column chromatography for purification (SiO2, eluent: dichloromethane/heptane 1/1). The compound was washed with hot heptane in a glass filter an dried under vacuum. Compound 2436 (1.0 g, 48%) was obtained as a yellow solid. M+H=632.2. $\lambda_{max}$ (ethyl acetate) 437 nm, $\epsilon$=19300 and 450 nm, $\epsilon$=19000. $\lambda$(em) (ethyl acetate) 499 nm.

We tested the lifetime of various molecule in a PET (polyethylene terephthalate) film by measuring the lifetime under illumination with blue light at 0.5-7 W/cm² at 60° C. The concentration and the thickness of the layers were set so that the transmission of blue light was 90%. All dyes in the PET film showed a PLQE (photoluminescent quantum efficiency) between 0.92 and 0.96.

The lifetime is determined as 10% reduction extrapolated to the conditions for a TLED (0.016 W/cm² blue and a temperature of 60° C. in air) assuming a linear dependence on the flux density. In the case of F083 a lifetime of about 100 hours was estimated while new compound 2363 showed a lifetime of about 2500 hours. This means an increase in lifetime of about 25 times. For new compound 2389 the lifetime is further increased with another factor of about 5 to 12500 hours under the same conditions. For new compound 2401 the lifetime is even further increased with another factor of about 10 to 27000 hours under the same conditions Lifetime of organic yellow emitting molecules in a PET matrix (in hours at which 10% has bleached at an exposure of 0.016 W/cm² blue and a temperature of 60° C. in air)

| F083 | F170 | Solvent yellow 98 | 2363 | 2389 | 2401 | 2402 | 2413 | 2436 |
|---|---|---|---|---|---|---|---|---|
| 50-200 | 150-400 | 400-650 | 2500-2800 | 10000-15000 | 27000 | 14000 | 6000 | 12000 |

Examples of White Blends

Example 1

Emission of various organic molecules excited by blue LED can be combined to produce white light. Herein, the emission from the molecules depicted in FIGS. 4a (material 2389, see FIGS. 2b) and 4b (N,N'-Bis(2,6-diisopropylphenyl)-1,7-di(2,6-diisopropylphenoxy)perylene-3,4:9,10-tetracarboxdiimide; Cas nr. 919488-78-1), were combined with blue light to obtain white light with a spectrum shown in FIG. 4c. Such a white light can be produced showing the following values shown in the table below.

Example 2

Figure 4A:
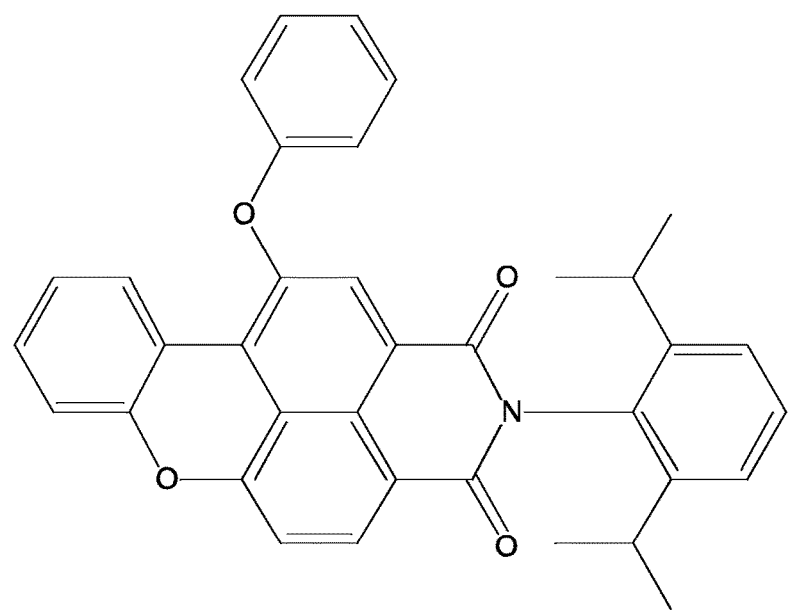
FIG. 4a-4b depicts a number of organic luminescent materials for creating luminescence spectra, as shown in FIGS. 4c-4d.
Figure 4B:
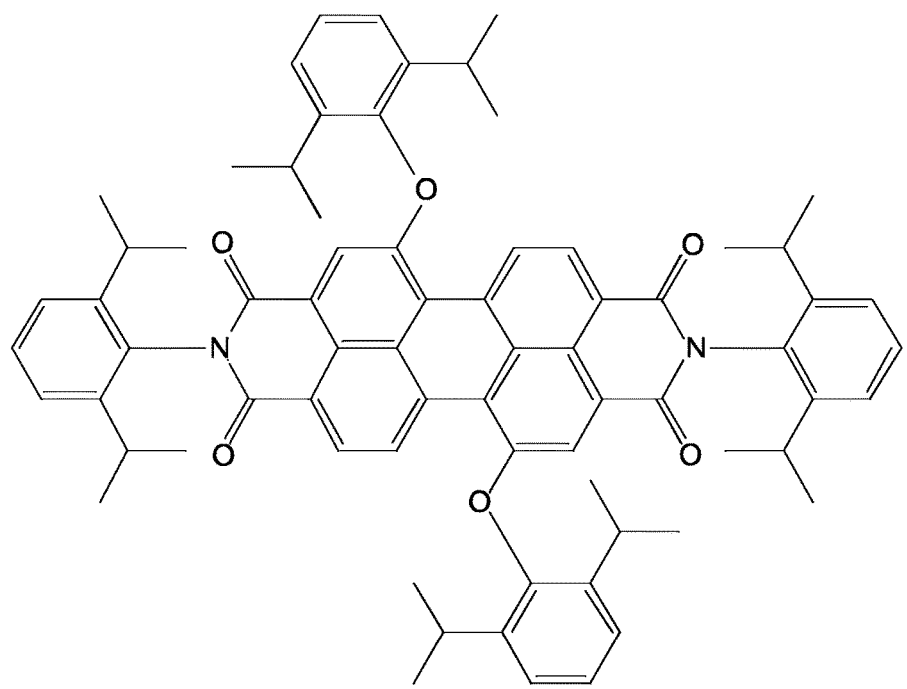
Figure 4C:
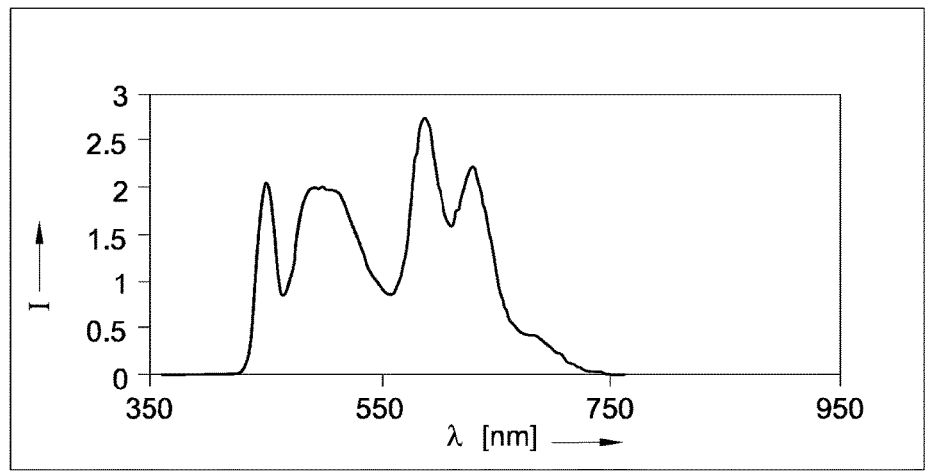
Figure 4D:
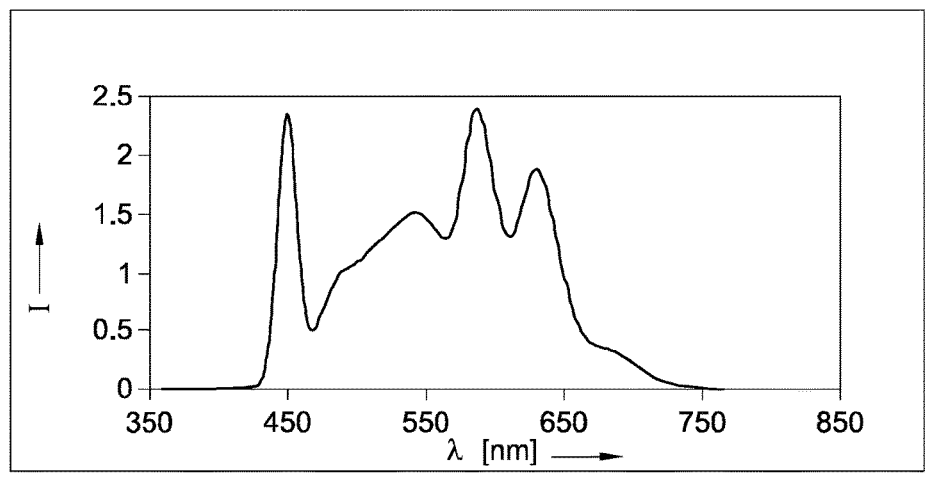

In this example the emission from the molecules depicted in FIGS. 4a and 4b were combined with blue light and also with emission from a inorganic phosphor thiogalate ($SrGa_2S_4:Eu^{2+}$) to obtain white light with a spectrum shown in FIG. 4d, and with values as shown in the table below.

|  | Conversion efficiency (Lm/W optical blue) | CCT | CRI | R9 |
|---|---|---|---|---|
| Example 1 | 243 | 4015 | 81 | 63 |
| Example 2 | 265 | 4016 | 86 | 22 |

Figure 5:
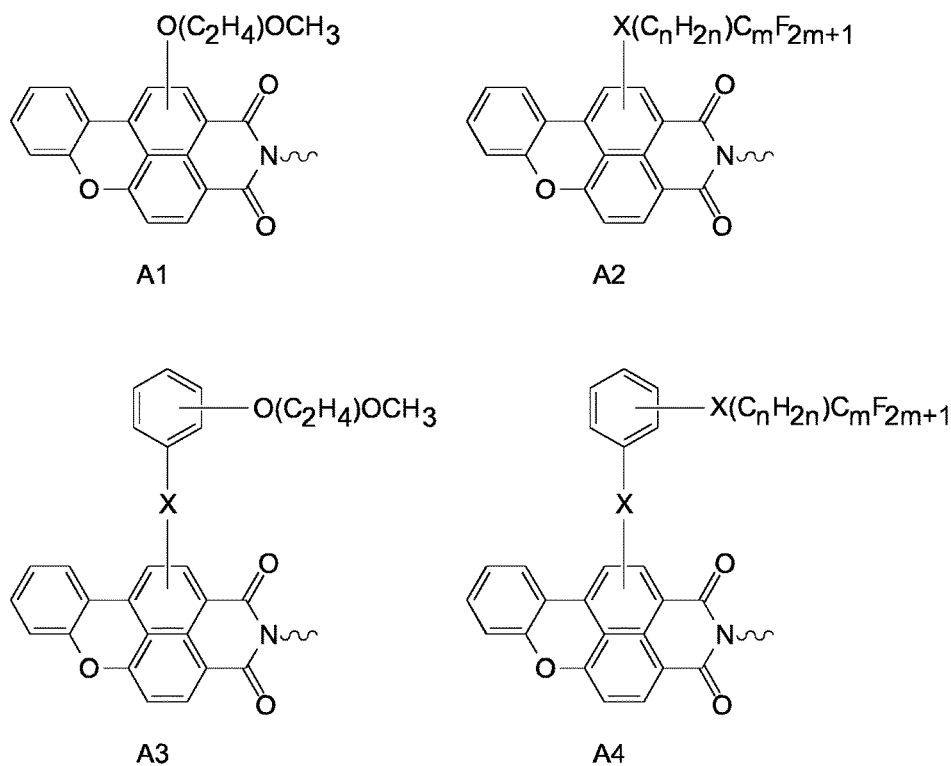
FIG. 5 depicts examples of further organic luminescent materials.

Further examples of organic luminescent materials according to formula I are depicted in FIG. 5. Herein, X may relate to a C—C bond or to an oxygen, i.e. an ether bond. By way of Example, one or more of $G_2$ and $G_3$ comprise groups which include ether groups or which groups are fluorinated with one or more fluor substituents, or $G_2$ and/or $G_3$ comprise Y groups, with one or more of D, E, I, L and M comprising alkyl groups which include ether groups or which groups are fluorinated with one or more fluor substituents. The organic molecules depicted in FIG. 5 are amongst others provided as examples. Other examples, with other groups or groups located elsewhere may also be possible.

The invention claimed is:

1. A lighting device comprising (a) a light source configured to generate light source light, and (b) a light converter configured to convert at least part of the light source light into visible converter light, wherein the light converter comprises a matrix containing an organic luminescent material as defined by formula (I):

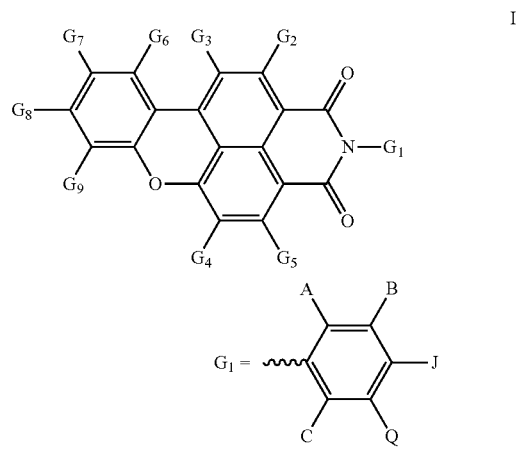

with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl;

in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl; and wherein one or more of A, B, C, J, and Q independently comprise isopropyl or tertbutyl and wherein $G_8$ does not include an amine group.

2. The lighting device according to claim 1, wherein two of A, B, and C are independently selected from the group consisting of isopropyl and tertutyl.

3. The lighting device according to claim 2, wherein one or both of $G_3$ and $G_4$ are independently selected from $R_3$ and $OR_3$, wherein $R_3$=Y, with Y being defined according to the following structure:

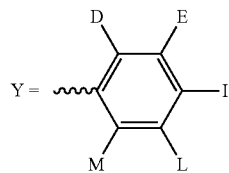

with D, E, I, L and M independently being selected from hydrogen, halogen, $R_5$, $OR_5$, $NHR_5$, and $NR_6R_5$, wherein $R_5$ and $R_6$ are independently selected from $C_1$-$C_{18}$alkyl, $C_6$-$C_{24}$aryl, and $C_6$-$C_{24}$heteroaryl.

4. A lighting device comprising (a) a light source configured to generate light source light, and (b) a light converter configured to convert at least part of the light source light into visible converter light, wherein the light converter comprises a matrix containing an organic luminescent material as defined by formula (I):

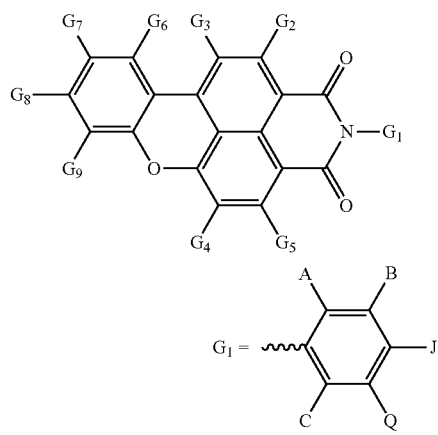

with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl;

in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl; and wherein one or more of A, B, C, J, and Q independently comprise isopropyl or tertbutyl, and wherein either (i) A and C are isopropyl, wherein $G_2$, $G_5$, $G_7$-$G_9$, B, J and Q are hydrogen, or wherein (ii) B and C are tertbutyl, wherein $G_2$, $G_5$, $G_7$-$G_9$, A, J and Q are hydrogen.

5. The lighting device according to claim 4, wherein one or both of $G_3$ and $G_4$ are independently selected from $R_3$ and $OR_3$, wherein $R_3$=Y, with Y being defined according to the following structure:

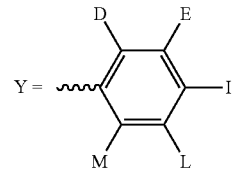

with D, E, I, L and M being hydrogen.

6. The lighting device according to claim 1, wherein one or more of $R_1$, $R_2$, $R_3$, $R_4$, $R_5$, $R_6$, $R_7$ are available, one or more of these are independently selected from the group consisting of (i) $C_nH_{2n}$+1Om, with n being an integer from 1 to 18 and with $0 \le m \le n/2$, (ii) -$C_nH_{2n+1}$- mFm with n being an integer from 1 to 18 and with $0 \le m \le 2n+1$, (iii) $C_6$-$C_{24}$aryl comprising one or more ether groups, (iv) $C_6$-$C_{24}$aryl comprising one or more fluor substituents, (v) $C_6$-$C_{24}$heteroaryl comprising one or more ether groups, and (vi) $C_6$-$C_{24}$heteroaryl comprising one or more fluor substituents.

7. A lighting device comprising (a) a light source configured to generate light source light, and (b) a light converter configured to convert at least part of the light source light into visible converter light, wherein the light converter comprises a matrix containing an organic luminescent material as defined by formula (I):

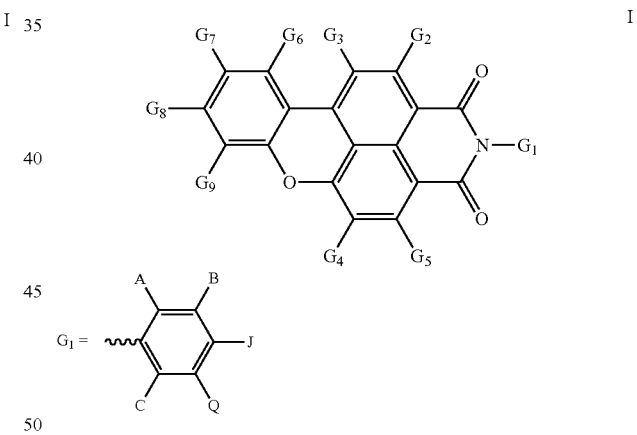

with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl;

in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryl; and wherein one or more of A, B, C, J, and Q independently comprise isopropyl or tertbutyl, and wherein the lighting device further comprises a further luminescent material configured to provide red light, wherein the further luminescent material comprises an organic luminescent material as defined by formula (II):

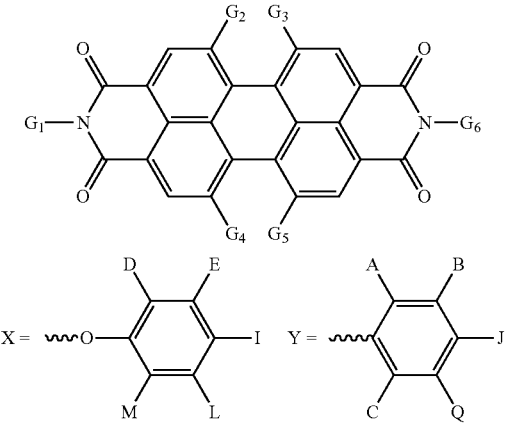

in which:
- $G_1$ and $G_6$ independently comprise a group selected from a linear alkyl, a branched alkyl, an oxygen-containing alkyl, a cycloalkyl, a naphtyl, and Y;
- wherein each of A, B, C, J and Q independently comprise a group selected from hydrogen, fluorine, chlorine, isopropyl, t-butyl, methoxy, an alkyl with up to 16 carbon atoms, and an oxygen containing alkyl with up to 16 carbon atoms;
- $G_2$, $G_3$, $G_4$ and $G_5$ independently comprise a group selected from hydrogen, fluorine, chorine, isopropyl, t-butyl, methoxy, alkyl with up to 16 carbon atoms, and oxygen-containing alkyl with up to 16 carbon atoms, and X;
- wherein each of D, E, I, L and M independently comprise a group selected from hydrogen, fluorine, chlorine, isopropyl, t-butyl, methoxy, alkyl with up to 16 carbon atoms, and an oxygen-containing alkyl with up to 16 carbon atoms;
- and in which at least two selected from $G_2$, $G_3$, $G_4$, and $G_5$ at least comprise X, wherein independently at least one of D, E, I, L and M of at least two of said at least two selected from $G_2$, $G_3$, $G_4$, and $G_5$ comprise a group selected from fluorine and chlorine, especially fluorine.

8. The lighting device according to claim 1, wherein the light source is configured to provide blue light, wherein the lighting device further comprises a further luminescent material configured to provide red light, wherein the further luminescent material comprises a luminescent material selected from the group consisting of (Ba,Sr,Ca)S:Eu, (Mg,Sr,Ca)AlSiN$_3$:Eu, (Ba,Sr,Ca)$_2$Si$_5$N$_8$:Eu and a quantum dot based luminescent material.

9. The lighting device according to claim 1, wherein the matrix comprises an aromatic polyester or a copolymer thereof.

10. The lighting device according to claim 1, wherein one or more of $G_1$, $G_2$, $G_3$, $G_4$, $G_5$, $G_6$, $G_7$, $G_8$ and $G_9$, comprise a covalent link with the matrix.

11. A light converter comprising a matrix containing an organic luminescent material as defined by formula (I):

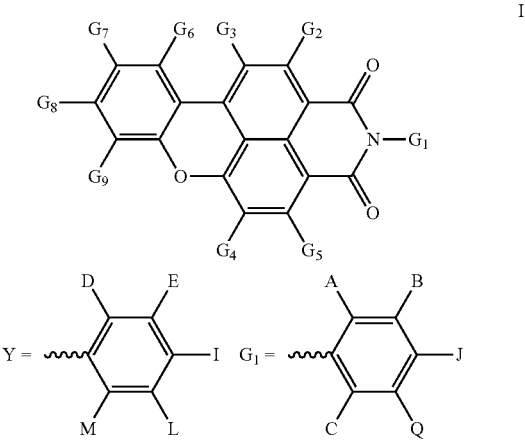

with $G_1$ as defined above, in which A, B, C, J, Q are independently selected from hydrogen, halogen, $R_1$, $OR_2$, $NHR_7$, and $NR_2R_7$, wherein $R_1$ is independently selected from $C_2$-$C_{18}$alkyl, $C_6$-$C_{24}$aryl, and $C_6$-$C_{24}$heteroaryl; and wherein $R_2$ and $R_7$ are independently selected from $C_1$-$C_{18}$alkyl, $C_6$-$C_{24}$aryl, and $C_6$-$C_{24}$heteroaryl;

in which $G_2$-$G_9$ are independently selected from hydrogen, halogen, $R_3$, $OR_3$, $NHR_3$, and $NR_4R_3$, wherein $R_3$ and $R_4$ are independently selected from $C_1$-$C_{18}$alkyl, $C_6$-$C_{24}$aryl, and $C_6$-$C_{24}$heteroaryt and wherein one or more of A, B, C, J, and Q independently comprise isopropyl or tertbutyl; and wherein one or both of $G_3$ and $G_4$ are independently selected from $R_3$ and $OR_3$, wherein $R_3$=Y, with D, E, I, L and M being hydrogen, and wherein $G_2$, $G_5$, $G_7$-$G_9$, J and Q are hydrogen.

12. The light converter according to claim 11, wherein the matrix comprises polyethylene terephthalate (PET), and wherein the matrix comprises a further luminescent material embedded in the matrix.

* * * * *